United States Patent [19]

Albert

[11] 4,323,779

[45] Apr. 6, 1982

[54] SCANNING RADIOGRAPHIC METHOD

[76] Inventor: Richard D. Albert, 317 Hartford Rd., Danville, Calif. 94526

[21] Appl. No.: 100,422

[22] Filed: Dec. 5, 1979

Related U.S. Application Data

[62] Division of Ser. No. 803,077, Jun. 3, 1977, Pat. No. 4,196,351.

[51] Int. Cl.$^3$ .............................................. H05G 1/26
[52] U.S. Cl. ................................................... 250/401
[58] Field of Search ................. 250/401, 416 TV, 521; 358/111

[56] References Cited

U.S. PATENT DOCUMENTS

| | | | |
|---|---|---|---|
| 2,477,307 | 7/1949 | Mackta | 358/111 |
| 2,638,554 | 5/1953 | Bartow et al. | 250/416 TV |
| 2,730,566 | 1/1956 | Bartow et al. | 250/416 TV |
| 2,777,068 | 1/1957 | Bowser | 250/521 |
| 3,852,605 | 12/1974 | Watanabe et al. | 250/416 TV |
| 3,949,229 | 4/1976 | Albert | 250/416 |
| 4,002,917 | 1/1977 | Mayo | 250/445 T |
| 4,032,787 | 6/1977 | Albert | 250/402 |
| 4,057,733 | 11/1977 | Hofmockel et al. | 250/521 |
| 4,057,745 | 11/1977 | Albert | 313/55 |
| 4,239,971 | 12/1981 | Cushman | 250/416 TV |

FOREIGN PATENT DOCUMENTS 1163107  9/1969  United Kingdom ................ 358/111

*Primary Examiner*—Davis L. Willis

[57] ABSTRACT

Visual display of dental, medical or other radiographic images is realized with an X-ray tube in which an electron beam is scanned through an X-Y raster pattern on a broad anode plate, the scanning being synchronized with the X-Y sweep signals of a cathode ray tube display and the intensity signal for the display being derived from a small X-ray detector which receives X-rays that have passed through the subject to be imaged. Positioning and support of the detector are provided for by disposing the detector in a probe which may be attached to the X-ray tube at any of a plurality of different locations and by providing a plurality of such probes of different configuration in order to change focal length, to accommodate to different detector placements relative to the subject, to enhance patient comfort and to enable production of both periapical images and wider angle pantomographic images. High image definition with reduced radiation dosage is provided for by a lead glass collimator situated between the X-ray tube and subject and having a large number of spaced-apart minute radiation transmissive passages convergent on the position of the detector. Releasable mounting means enable changes of collimator in conjunction with changes of the probe to change focal length. A control circuit modifies the X-Y sweep signals applied to the X-ray tube and modulates electron beam energy and current in order to correct for image distortions and other undesirable effects which can otherwise be present in a scanning X-ray system.

6 Claims, 18 Drawing Figures

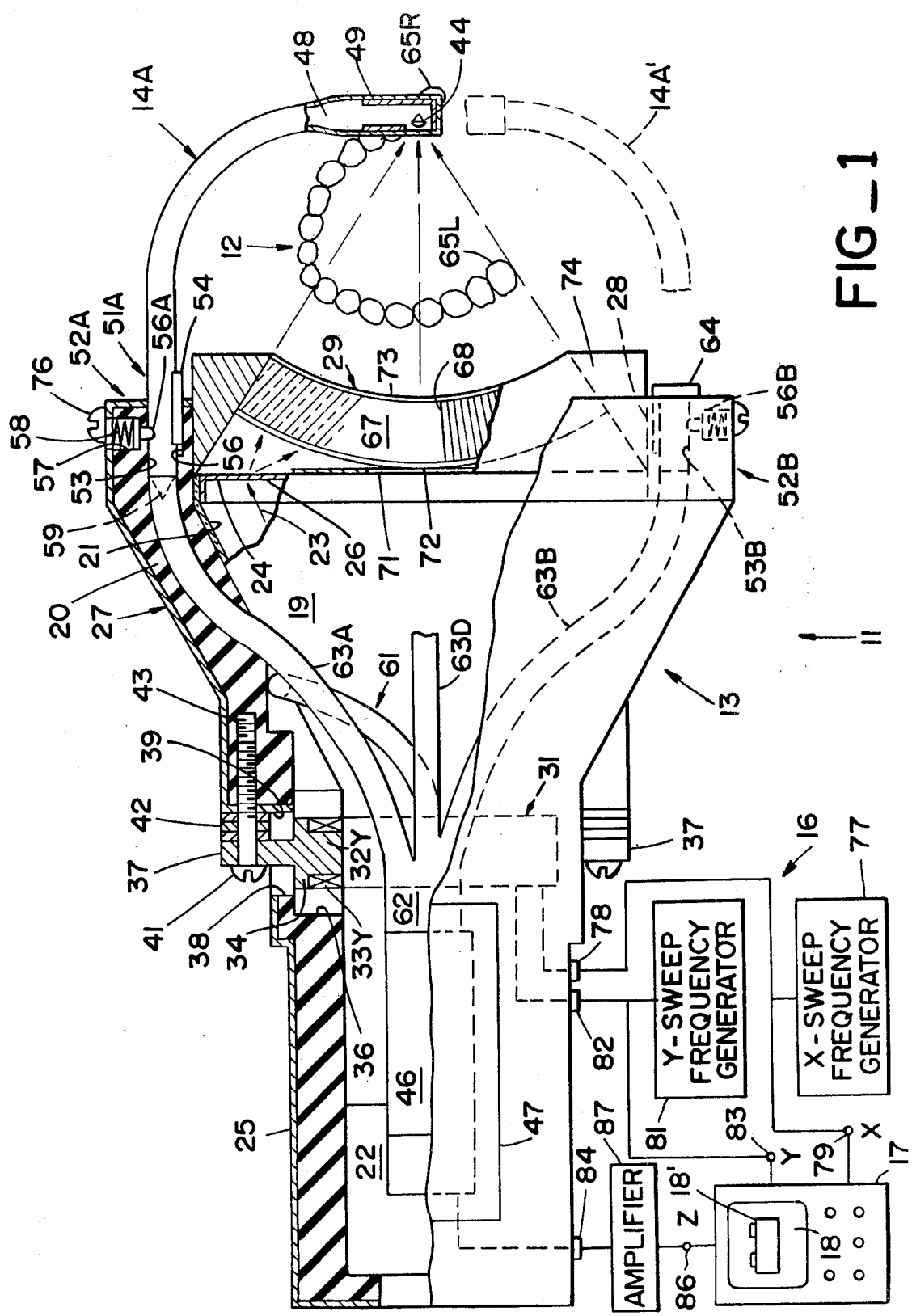
FIG_1

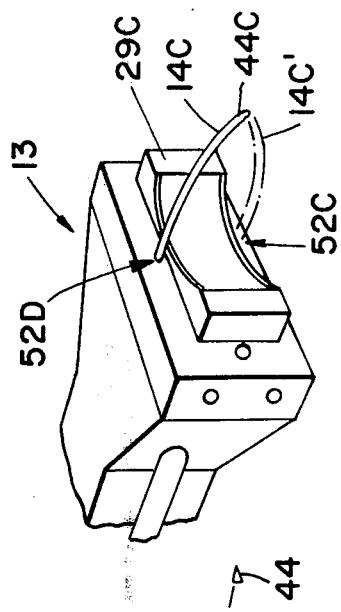
FIG_8
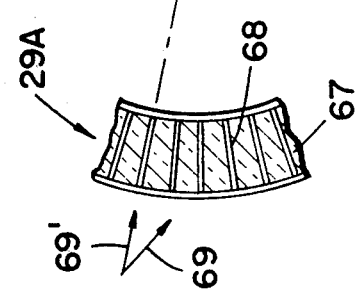
FIG_6
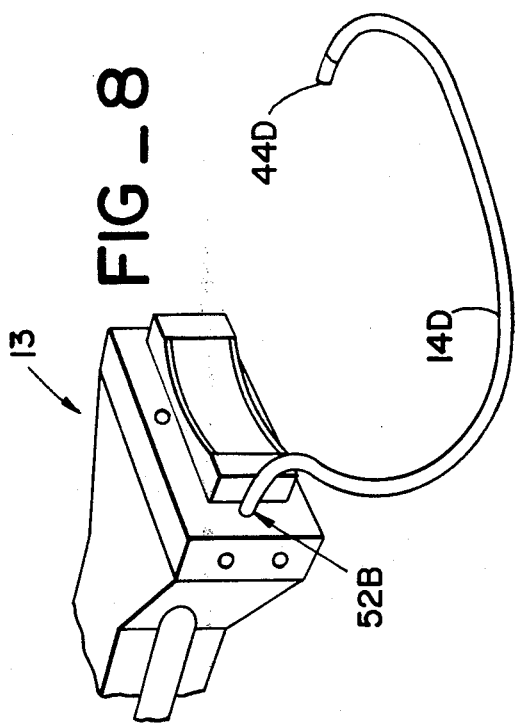
FIG_2
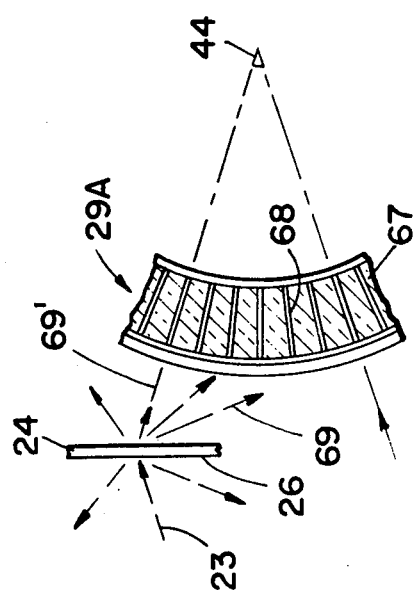
FIG_4
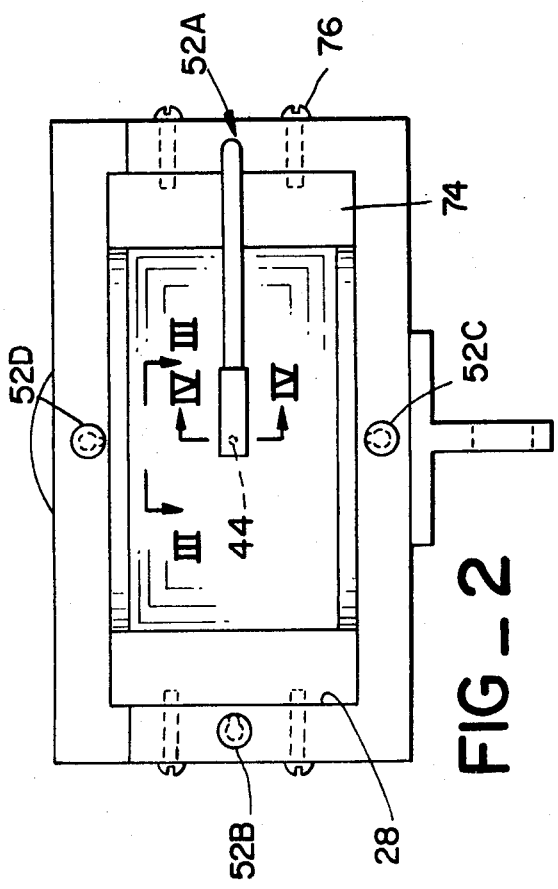
FIG_3

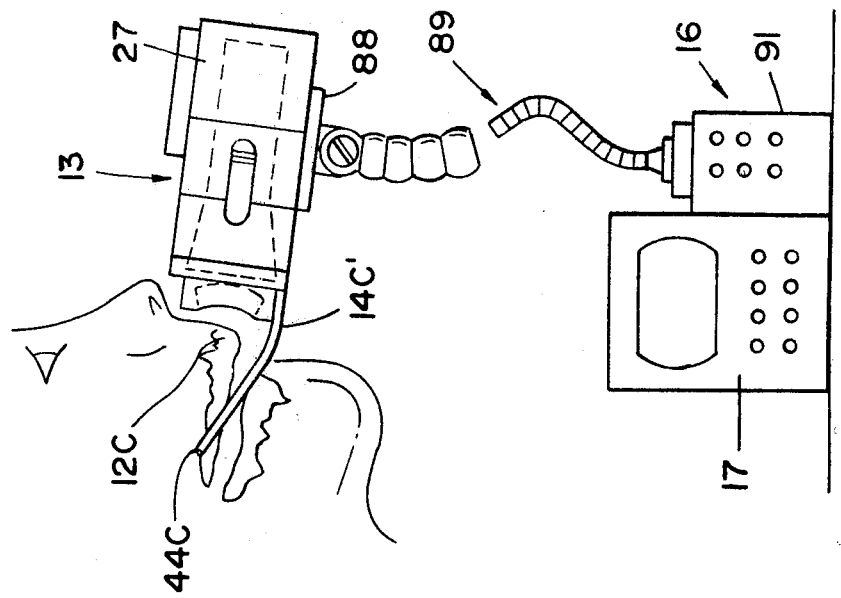
FIG_7
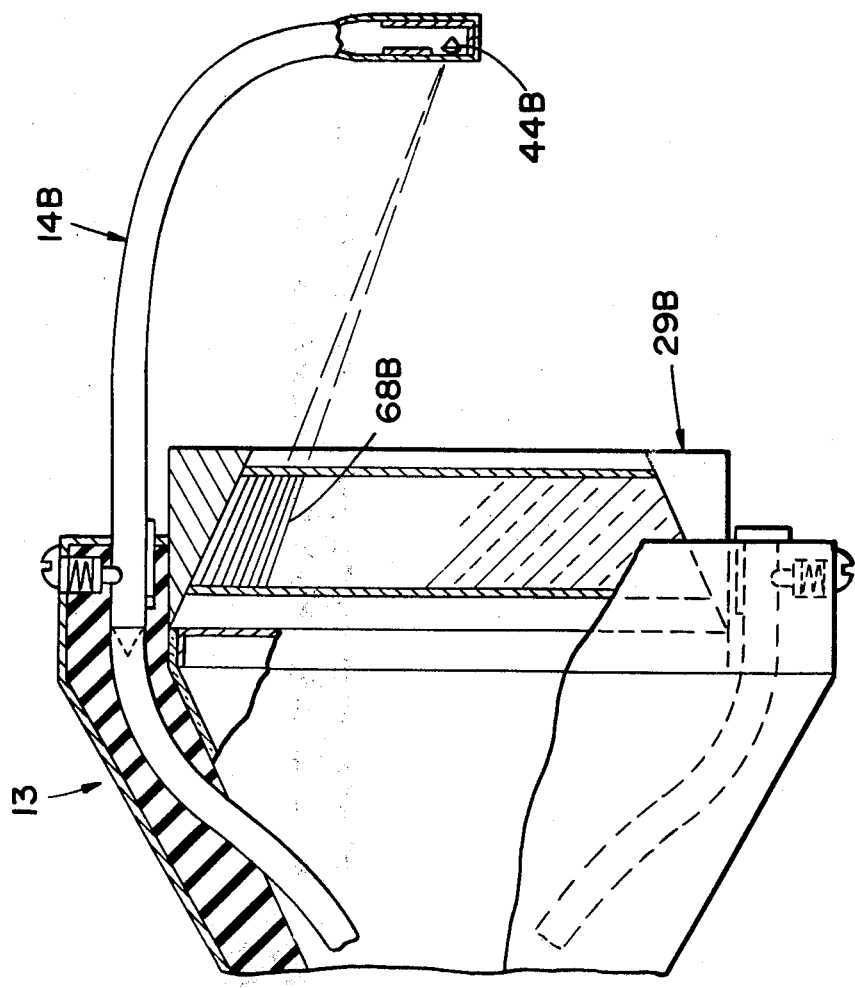
FIG_5

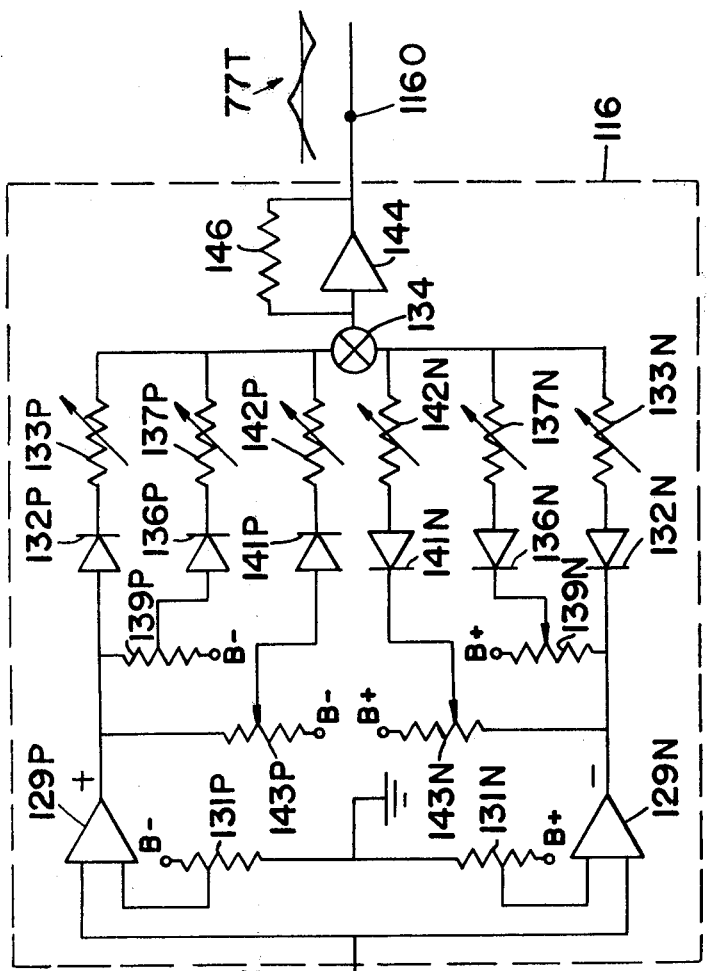
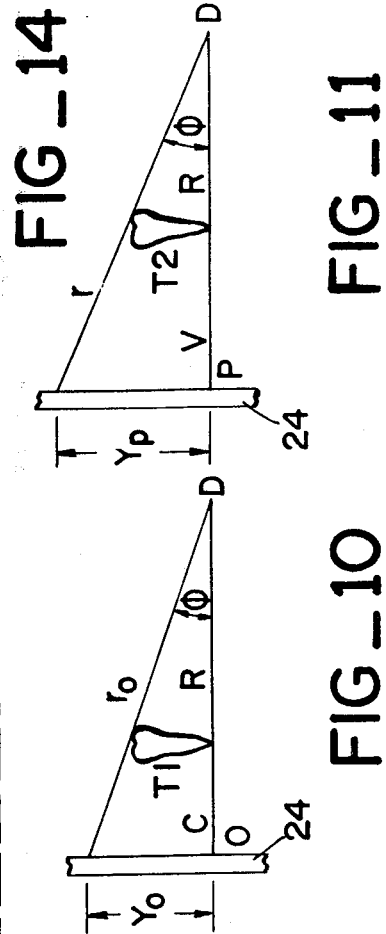
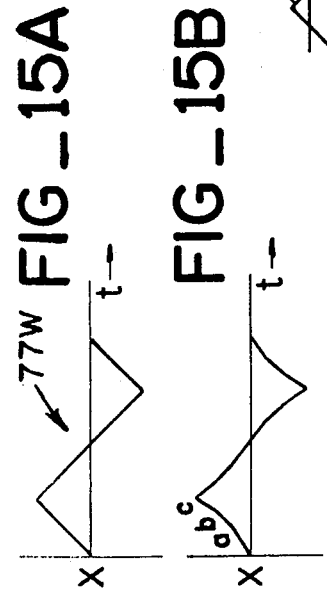
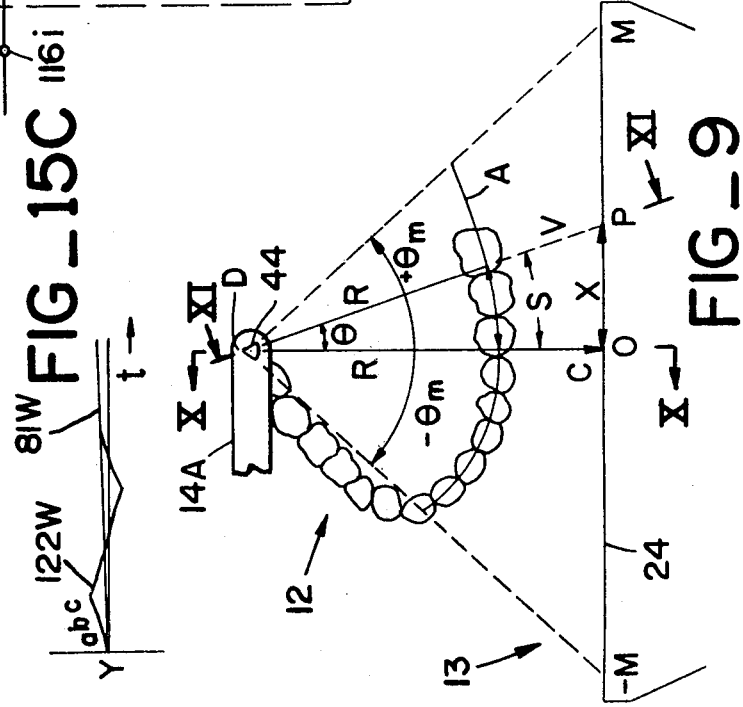

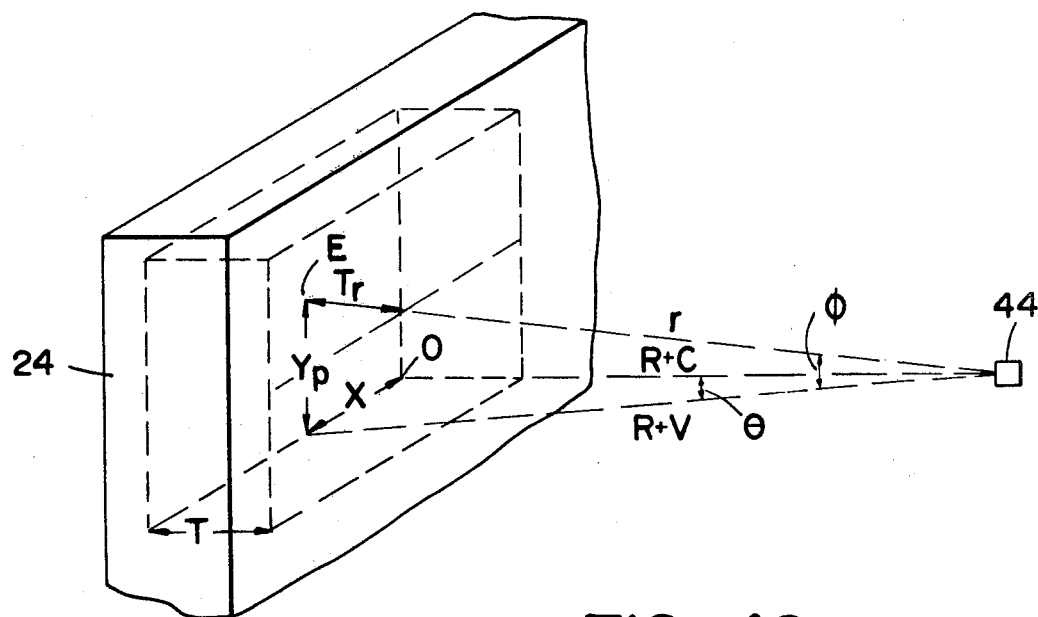
FIG_12
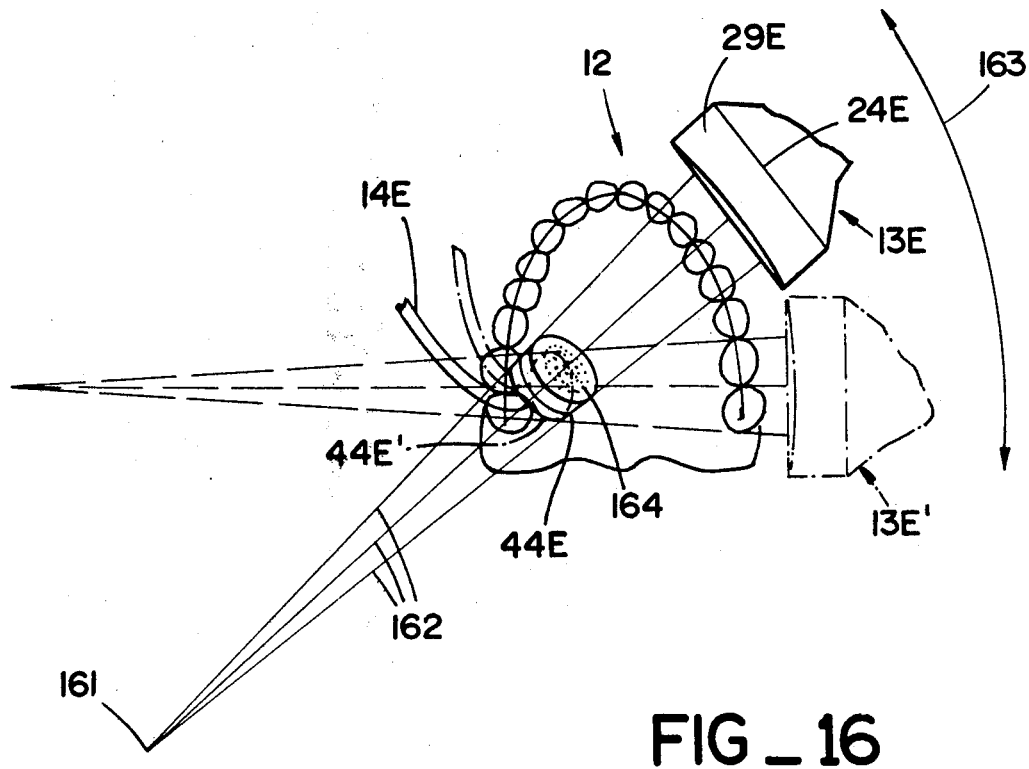
FIG_16

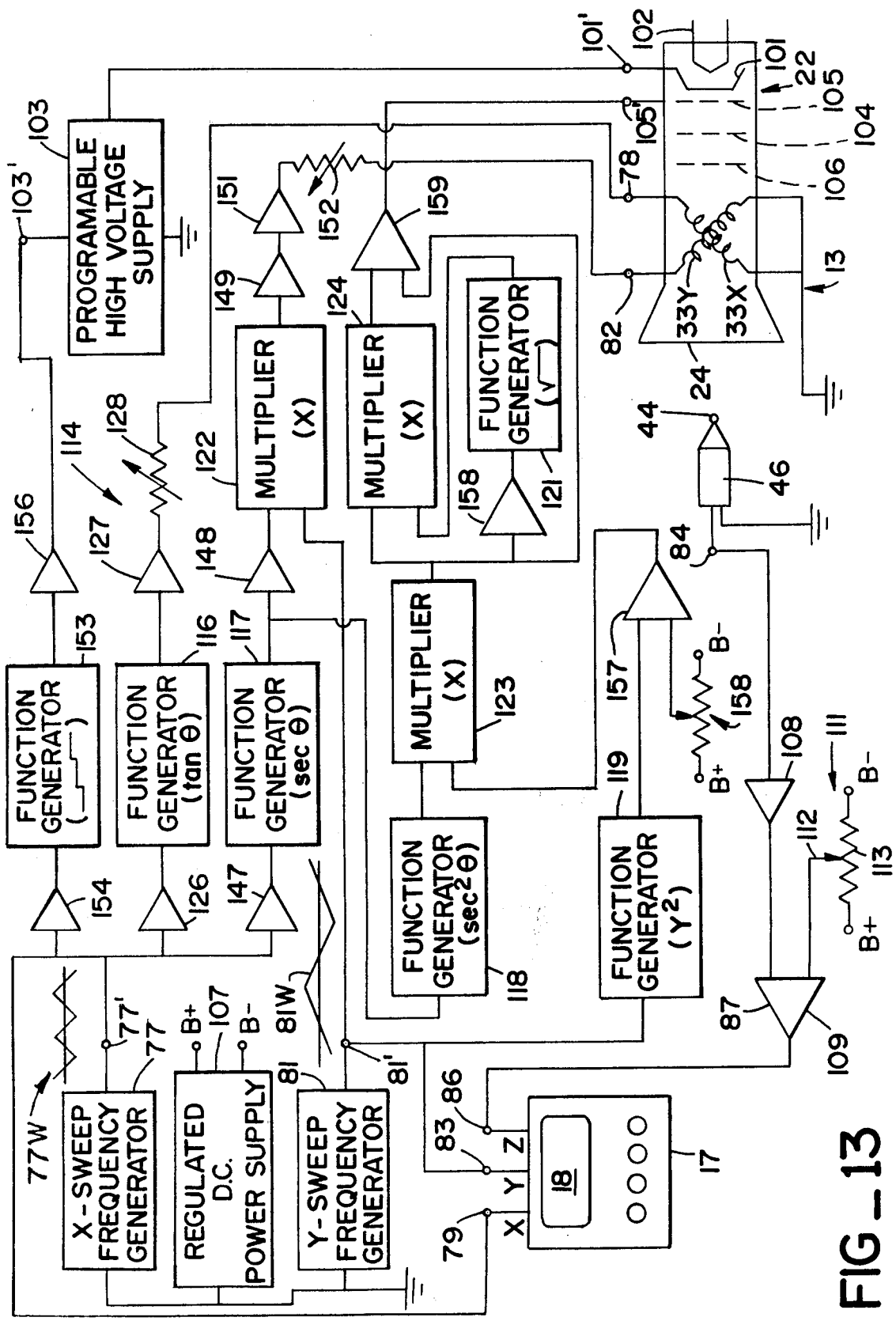
FIG_13

SCANNING RADIOGRAPHIC METHOD

This is a divisional application of applicant's prior application Ser. No. 803,077 filed June 3, 1977 now issued as U.S. Pat. No. 4,196,351.

BACKGROUND OF THE INVENTION

This invention relates to radiographic apparatus and procedures and more particularly to scanning X-ray systems which produce signals which may be used to present a visible image at a cathode ray tube screen or the like.

The present invention was initially developed for usage in dental and medical radiology, and to facilitate description the invention will be herein discussed with reference to this particular field of use. As will be apparent, the apparatus may also be advantageously adapted to various other radiographic operations.

The procedure which has been most commonly used by dentists to obtain radiographic images of the teeth, jaw structure or the like of patients produces what is called a periapical X-ray radiograph. In this known procedure an X-ray film packet is inserted into the patient's mouth near the teeth or other anatomical structure to be imaged. The procedure makes use of an X-ray tube of the form which generates X-rays at a fixed point on an anode and in which the X-rays radiate out from that fixed point. The tube is provided with a shield cone which is directed at the film packet through the teeth or other structures to be imaged. Precise positioning of both the film packet and the shield cone is necessary to obtain useful X-ray images.

Although the conventional periapical X-ray procedure is very extensively used, it is subject to several serious disadvantages. The need to insert and retain a relatively large film packet in a patient's mouth, for example, often causes discomfort or gagging and may not be tolerable to certain patients such as small children and elderly persons. Further, no visible image is available to the dentist until the film packet has been removed and subjected to time-consuming development procedures. An instantaneous radiographic image can be much more useful to the dentist.

Another very serious problem is that undesirably large radiation dosage exposures of the patient are needed in order to produce a complete set of dental X-ray images. This is in part a result of the very low detection efficiency of the unscreened X-ray film commonly used for dental X-ray operations.

Techniques for reducing radiation exposure have heretofore been developed utilizing screened film in which detection efficiency is greatly improved by disposing an image-intensifying phosphorescent material in contact with the X-ray film emulsion surface. Owing to several disadvantages of its own, such as reduced image definition, the screened film procedure has not proved to be practical in many situations.

The problem of high radiation exposure in dental radiology is often aggravated by a need to repeat the X-ray imaging process. It may be found that the critical alignment requirements were not met during the original exposure or errors in developing the exposed X-ray film may be made, both of which are fairly common occurrences.

In part to alleviate the radiation exposure problem, another procedure known as the pantomographic image technique has been developed and has been extensively utilized in the recent past by dentists and oral surgeons. In this procedure panoramic or wide angle X-ray images are produced by generating a narrow linear X-ray beam which is revolved during the exposure about an axis of rotation situated within the patient's head. The X-ray tube is essentially a conventional one at which X-rays are generated at a small fixed point on an anode. Radiation generated at this point is collimated by a first slit which is parallel to the axis of rotation and then passes through the patient's head and then through a second similar collimating slit situated in front of a screened film cassette which is rotated in synchronism with the rotational movement of the X-ray beam. The tube and detector motion causes the X-ray beam to sweep across the intervening anatomical structures. Upon development of the film, a panoramic two-dimensional strip image is produced of curved anatomical structures in the patient's head such as the mandible or maxilla.

Although a significant reduction of patient radiation dosage may be realized in comparison with periapical procedures, the conventional pantomographic image technique is itself subject to several disadvantages. It is necessary that the X-ray beam pass through the entire skull of the patient, even if it is only desired to obtain an image of a portion of the skull such as the dental arch. Consequently, unwanted images are superimposed upon the desired image data. This makes interpretation of the image more difficult and detracts from the general quality of the image by obscuring desired data to some extent with undesired information. Moreover, radiation exposure remains undesirably high as the X-ray beam must necessarily penetrate through the entire skull. Anatomical structures which are not of particular interest are thereby necessarily subjected to radiation dosage which dose not contribute any useful information but instead detracts from the quality of the desired data. Further a significant amount of X-ray scattering occurs during passage of the X-ray beam through the patient's entire head creating a background fog in the image on the developed film which undesirably limits the range of contrast in the image and which may cause loss of definition.

Additional losses of definition and contrast arise from the presence of the intensifying screen in front of the X-ray film. Underlying and supplementing these contrast limitations peculiar to the pantomographic image technique is the undesirably limited grey scale latitude of X-ray film in general. Still further, a long exposure time, typically about 20 seconds, is needed to complete a full mouth pantomographic image. As a result, problems often arise from patient motion or equipment vibration with consequent blurring of the resulting X-ray images. This tends to be particularly severe when the patient is an infant or young child. Finally, a considerable degree of distortion of the depicted objects is normally present in the conventional pantomographic image.

A radically different form of radiographic imaging system that alleviates or eliminates much of the disadvantages of prior techniques and apparatus is disclosed in applicant's U.S. Pat. No. 3,949,229 and applicant's copending application Ser. No. 663,988 filed Mar. 4, 1976 now U.S. Pat. No. 4,057,745. Applicant's copending application Ser. No. 674,059, filed Apr. 5, 1976, now U.S. Pat. No. 4,144,457, and Ser. No. 673,908, also filed Mar. 4, 1976, now U.S. Pat. No. 4,032,787, are also directed to scanning X-ray systems of this general kind.

The general form of scanning X-ray system disclosed in the above-identified prior patent and copending applications dispenses with the use of film as an X-ray detection medium and produces signals which may be used to produce a visible image on the screen of a cathode ray tube display device including instantaneous images if desired. Radiation dosage of the patient is substantially reduced. The system may be utilized to image only a selected portion of a subject such as a patient's dental arch for example without including superimposed data from other regions of the subject. Image data may be electronically stored on magnetic tape or by any of various other data storage means and the image data may also readily be processed by various electronic enhancement techniques to further improve image quality or to emphasize specific image characteristics.

A system of the general type described in the above-described patent and copending applications uses a scanning X-ray tube in which an electron beam is systematically swept in a raster pattern on a broad target or anode plate to produce a moving point source of X-rays. The region of the subject which is to be imaged is situated between the anode plate of the X-ray tube and an X-ray detector which is small in relation to the size of the raster pattern and which may therefore readily be situated in the oral cavity or the like of a dental or medical patient or in similarly constricted interior spaces of an inanimate subject. The raster sweep signals of a cathode ray tube display are coordinated with the scanning action of the electron beam in the X-ray tube and a signal derived from the X-ray detector output is applied to the intensity signal terminal of the cathode ray tube. As a result, a visible radiographic image of the region of the subject situated between the X-ray source and the detector is produced on the screen of the display device.

In order to be most useful for dental and medical usages and for certain other radiological operations where similar problems may be encountered, a scanning X-ray system of this general type should possess certain specific capabilities. First, radiation dosage should be minimized to the extent possible while producing an image of high definition and contrast range. Second, the dentist or other operator should be able to position the X-ray detector very precisely relative to the X-ray tube at any of a plurality of different positions within the patient's mouth, or in other constricted spaces, with a minimum of difficulty and with maximum patient comfort.

Further, it is highly desirable that the effective focal length of the system be readily and precisely changeable in order to obtain images of different degrees of magnification.

Still further, such a system should minimize optican distortions and other forms of image degradation, which can be present in apparatus of this general form, in order to facilitate image interpretation.

SUMMARY OF THE INVENTION

This invention is a scanning X-ray system for producing signals that may be used to present high-quality radiographic images on the screen of a cathode ray tube with relatively low radiation dosage of the subject and having structural provisions which greatly facilitate the obtaining of radiographs of different forms and radiographs taken from different locations, including locations within a patient's body or other constricted areas, with a single X-ray tube and accessories.

The X-ray tube has an electron gun, a broad target anode plate and deflector means for sweeping the electron beam on the anode plate to produce a moving X-ray origin point. An X-ray detector is positioned in spaced-apart relationship to the X-ray tube on the opposite side of the portion of a subject which is to be radiographed. The detector then produces output signals indicative of variations of radiation transmissiveness within the region of the subject which is scanned by the moving X-ray origin point. Raster scanning at a cathode ray tube may be coordinated with the scanning action of the X-ray tube while the intensity of the cathode ray tube display is modulated by the X-ray detector output signals to produce the desired visible radiographic image on the screen of the cathode ray tube.

In one aspect, the invention greatly facilitates the positioning and support of the X-ray detector at any of a variety of different positions in the oral cavity of a dental patient or at any of various other internal or external positions relative to a dental patient, a medical patient or an inanimate object which is to be imaged. For this purpose a series of X-ray detectors are provided, each being situated within a separate one of a series of long narrow probes of different lengths and configurations. Each probe has a base end releasably engageable in an attachment means situated on the X-ray tube and which contains means for receiving output signal data from the detector through the probe. Emplacement of a detector at any of a variety of different positions in or adjacent to a patient or other subject is then easily and quickly accomplished by selecting an appropriate one of the series of probes of different length and configuration. Adaptability of the system to production of any of a variety of different radiographs of different regions of the subject may be still further enhanced by providing a plurality of the probe attachment means at different locations on the X-ray tube.

In another aspect, the invention provides for obtaining radiographic images with very low radiation dosage while providing high definition and high contrast in the image. A radiation collimator is disposed between the X-ray tube and the subject to absorb X-rays that are not directed towards the X-ray detector and therefore could not contribute meaningful data to the desired image. In a preferred and highly advantageous form the collimator is an element formed of lead glass or the like having a large number of very minute spaced-apart radiation-transmissive passages which have axes convergent at the position of the X-ray detector. Utilization of lead glass for the collimator enables the providing of a very large number of extremely small and closely spaced radiation-transmissive passages, thereby enhancing definition in the image, inasmuch as collimators of this kind can readily and economically be produced by fiber optical techniques. In a preferred form, a plurality of collimators are provided each being mountable at the face of the X-ray tube by disengageable positioning means. This enables quick changes of the focal length of the system, to provide for changing the degree of magnification, since one collimator may readily be removed and replaced with another in which the radiation passages are convergent on a more distant or a closer X-ray detector as might be desired. To shift the location of the detector itself in conjunction with such a change of collimator and focal length, the series of probes discussed above include a number of probes which situate the X-ray detector at differing distances from the X-ray tube as determined by the different convergence points of the collimators.

In still another aspect, the invention provides for the reduction or elimination of several forms of optical distortion and image degradation which can otherwise be present in portions of an image produced by a system of this general type and which can complicate the process of interpreting the image. Means are provided, for example, for delinearizing the scanning action of the electron beam within the X-ray tube to compensate for variable magnification effects at different portions of the image which can otherwise be inherent in the geometry of such a system. Further means may be provided to increase electron beam current in the X-ray tube as the beam moves away from a centered position on the anode plate. This compensates for the fact that X-rays traveling toward the detector must pass through an increasing amount of target material as the X-ray origin point moves away from the axis of the tube and may also be used to compensate for inverse square law attenuation of the X-ray beam. Still further, means may be provided to change the energy of the electron beam in the tube at different areas of the scanning raster to compensate for differences in radiolucence of different regions of the subject which is being imaged. Such a radiolucence change can arise, for example, from the pronounced difference in the thickness of the molar teeth of a dental patient as opposed to the more forward teeth in the dental arch.

The several aspects of the invention briefly described above are preferably jointly utilized in a single system and then coact to enable the production of high-quality images with very low radiation doses of the subject and further provide a high degree of adaptability of a single instrument to the production of different forms of image, and to different orientations of the X-ray tube and detector relative to a subject. However, each of the above-described aspects may also be utilized independently of the others in a scanning X-ray system in circumstances where all of the several advantages of the invention may not be required.

BRIEF DESCRIPTION OF THE DRAWINGS

In the accompanying drawings:

FIG. 1 is a broken-out view of a scanning X-ray system in accordance with the invention as utilized for dental radiography with portions of the X-ray tube and the detector probe being broken out to illustrate internal structure and with certain electrical circuit components of the system being shown in schematic form, FIG. 2 is a frontal view of the face of the scanning X-ray apparatus of FIG. 1, FIG. 3 is a diagrammatic sectional view of a portion of a radiation collimator used in the apparatus of FIGS. 2 and 3 better illustrating the construction and operational effects of the collimator, taken along line III—III of FIG. 2, FIG. 4 is another diagrammatic section view of the collimator of the apparatus of FIGS. 1 and 2 taken along line IV—IV of FIG. 2 at right angles to the plane of FIG. 3, FIG. 5 is a partially broken-out view of the forward portion of an X-ray tube essentially similar to that of FIGS. 1 and 2 illustrating how the focal length of the system may be selectively changed by replacement of the X-ray probe and X-ray collimator, FIG. 6 is a perspective view of the forward portion of an X-ray tube similar to that of FIGS. 1 and 2 but employing a modified form of detector probe particularly adapted for the production of periapical dental X-ray images, FIG. 7 further illustrates the utilization of the invention for the production of periapical dental X-rays, FIG. 8 is another perspective view of the forward portion of an X-ray tube essentially similar to that of FIGS. 1 and 2 illustrating the usage of a different form of X-ray detector probe mounted at a different location on the face of the X-ray tube, FIG. 9 is a diagram illustrating how certain optical distortions can arise in a scanning X-ray system in the absence of corrective mechanisms, FIG. 10 is a diagram further clarifying one form of optical distortion which can arise in a scanning X-ray system when the scan departs from the central axis of the system in a first or X direction, FIG. 11 is a diagram illustrating a related form of distortion which can arise in such a system as the scan departs from the central axis in an orthogonal or Y direction, FIG. 12 is a diagram illustrating how still other forms of distortion can arise in the absence of corrective provisions, FIG. 13 is a circuit diagram of electrical components of the scanning X-ray system of the preceding figures including distortion correction means, FIG. 14 is a circuit diagram illustrating an example of a suitable, more detailed circuit for certain components shown in block form in FIG. 13, FIG. 15A is a diagram illustrating the X axis sweep frequency wave form utilized for the X-ray tube and display device of the system of the preceding figures, FIG. 15B is a diagram illustrating a modification of the wave form of FIG. 15A, prior to application to the X-ray tube, in order to compensate for the form of optical distortion which can otherwise occur if a linear X axis sweep is utilized in the X-ray tube, FIG. 15C is a diagram illustrating a modification of the Y axis sweep wave form which is made to compensate for a form of distortion which can otherwise occur upon departure of the electron beam of the X-ray tube from the axis of the system in the Y scan direction, and FIG. 16 illustrates a modification of the X-ray tube and detector probe of the invention embodying still another means for alleviating image distortion effects.

DESCRIPTION OF PREFERRED EMBODIMENTS

Referring initially to FIG. 1 of the drawings, a scanning X-ray system 11 is shown which greatly facilitates the obtaining of a variety of different forms of dental radiograph including the providing of instantaneous high-quality images with relatively low radiation dosage of the patient. The apparatus is depicted in FIG. 1 as utilized to produce a pantomographic image of the left half of the lower dental arch of a subject 12. As will hereinafter be discussed, the same apparatus may then be quickly and conveniently adjusted to provide additional images for completing a set of pantomographic images, to provide one or more periapical images of individual teeth of particular interest and may also easily be used to produce images of other anatomical structures or of inanimate objects.

Salient components of the scanning X-ray system 11 include a scanning X-ray tube 13 of specialized construction, an X-ray detector probe 14A extending outwardly from the face of the tube and being supported thereby and an electrical control and signal processing circuit 16 including a cathode ray tube or other type of X-Y display device 17 of the form having a screen 18 at which visible images are displayed in response to X and Y axis sweep frequency signals received at terminals X and Y respectively and in response to intensity signals received at another terminal Z. Oscilloscopes, television receivers and the like of known construction may readily be utilized as the display device 17.

X-ray tube 13 includes a vacuum enclosure 19, formed of glass or other suitable electrically insulative material, which defines an evacuated region 21. Vacuum enclosure 19 has a relatively narrow end containing an electron gun 22 of suitable known construction for producing and accelerating an electron beam 23 towards an opposite target end of the enclosure. The target end of enclosure 19 is larger than the electron gun end and is preferably of rectangular configuration where the system is to be used primarily for dental X-ray operations. The target end of vacuum enclosure 19 is formed at least in part by a target anode plate 24 having at least an inner surface 26 consisting of one of the electrically conductive metals which produce X-rays upon being bombarded by high-energy electrons, copper, tungsten and tantalum being examples of metals suitable for the target anode surface 26. Contrast in the image is enhanced if the X-rays which reach the detector are monochromatic or nearly so. This may be arranged for by an appropriate selection of the thickness of the target anode plate 24 since elemental target materials tend to be more transmissive of their own characteristic X-rays than of other X-ray wavelengths.

Vacuum enclosure 19 is disposed within a housing 27 to support and protect the enclosure and to enable the mounting of additional components on the tube as will hereinafter be described. Housing 27 may be formed of radiation-absorbent material such as steel or of any of various known plastics which contain a sizable admixture of a heavy radiation-absorbent metal or, as in this example, of plastic having a layer 27' of radiation-absorber at the outer surface. As best seen by referring to FIG. 2 in conjunction with FIG. 1, housing 27 has a rectangular collimator receiving opening 28 in the region of the face of the tube which opening conforms in size and configuration with the target anode plate 26 of the tube. An X-ray collimator 29A, which will hereinafter be discussed in more detail, is received and supported in opening 28.

To generate a moving point source of X-rays, electron beam 23 is swept in a raster pattern on target anode plate 26. The electron beam movement includes a repetitive sweep movement back and forth across the anode surface 26 in a first direction which is parallel to the plane of FIG. 1, and which is herein designated the X-axis direction. At the same time, the electron beam is also swept at a slower rate back and forth in an orthogonal direction which in this example is normal to the plane of FIG. 1 and is herein designated the Y-axis direction. The combining of these two movements causes the electron beam to sweep successively along a series of substantially parallel lines which jointly define a rectangular raster pattern area on surface 26 of the anode plate. Sweeping of the electron beam in this manner is accomplished with deflector means which may be of known internal construction, an annular magnetic beam deflector 31 being utilized in this example. Magnet deflector 31 may be of the form having four magnetic poles angularly spaced in quadrature, of which a single pole 32Y and winding 33Y appears in FIG. 1, and having an annular ferromagnetic yoke 34 which encircles each of the poles. Deflector 31 is disposed coaxially around the vacuum enclosure 19 between the electron gun 22 and target anode plate 26 within an annular groove 36 in the inside surface of housing 27.

Under certain circumstances it may be desirable to selectively change the focal length of the scanning X-ray system by making certain adjustments which will hereinafter be explained in more detail. One adjustment which compensates for an optical distortion which could otherwise occur upon a change of focal length requires the providing of means for selectively shifitng the axial position of the area in which beam deflection occurs so that the beam deflection area may be moved further from target anode plate 26 or closer to the target anode plate. To enable such an adjustment in this example, the annular groove 36 in which deflector 31 is situated is of greater length along the axis of the tube than is the deflector itself so that the deflector may be moved in the axial direction towards the target anode plate 26 or toward the electron gun 32 as desired. To facilitate such movement of the deflector 31 and to hold the deflector at a selected axial position, tabs 37 extend radially outwardly from opposite sides of the deflector through slots 38 provided in housing 27 for that purpose. A boss 39 is formed on housing 27 adjacent the forward end of each slot 38 and one of a pair of disengageable screws 41 extends through each tab 37, through a series of annular washers 42 and engages in a threaded bore 43 in the adjacent boss 39.

Thus by temporarily disengaging screws 41 and adding or removing washers 42 as necessary, and then replacing the screws, the deflector 31 may be located and fixed at any desired axial position within the limits established by the length of groove 36. In instances where frequent changes of the axial position of the deflector 31 may be desirable, more quickly operated axial positioning means of any of various forms may be utilized in place of the screws 41, the threaded rotatable telescoping sleeve mechanisms commonly used for changing the focal length of photographic cameras by axial movement of lenses being one example. It should also be noted that while this example of the invention utilizes beam deflection means of the magnetic variety, electrostatic beam deflection may also be used.

Considering now a suitable construction for the probe 14A, X-rays produced at target anode plate surface 26 and transmitted through collimator 29A converge at a relatively small X-ray detector 44 situated at the distal end of the probe 14A at a location on the central longitudinal axis of the X-ray tube. The location of detector 44 is spaced from the face of the tube, including collimator 29A, to enable positioning of the subject 12 which is to be imaged between the collimator and detector. Thus X-rays received at the detector 44 must first pass through the anatomical region or the like which is to be imaged. Definition in the image is in part a function of the difference in size between the raster pattern area at target anode plate 26 and the radiation-sensitive area of the detector 44. Accordingly detector 44 should preferably have a radiation-sensitive area as small as possible consistent with the need to obtain an adequate count rate from the amount of radiation which is received. A form of radiation detector 44 highly suited for this purpose, in view of a very high detection efficiency and a minimum of structural complication, is a scintillation crystal of any of the known suitable forms such as sodium iodide doped with thallium, bismuth germanate or calcium fluoride. For clarity of illustration, the scintillation crystal detector 44 is necessarily depicted in FIG. 1 as being somewhat larger than is usually optimum in actual practice, crystals measuring less than one millimeter in size being typical. Scintillation crystals of this kind respond to individual X-rays by producing scintillations of visible light which may be converted to electrical X-ray count signals by photosensitive means. To further optimize definition in the image, detector scintillator 44 preferably is formed in the shape of a sector of a sphere and is situated coaxially with the axis of the X-ray tube with the apex of the sector being most distant from the X-ray tube and being at the point of convergence of the X-rays from target anode plate 26 that are transmitted through collimator 29A.

In addition to supporting and positioning the X-ray detector 44, the probe 14A also transmits the X-ray count signals produced by the detector to a photomultiplier tube 46 of known internal construction which in this example is situated adjacent the small end of vacuum enclosure 19 within housing 27, the housing having a protruding portion 47 formed to receive the photomultiplier tube. For this purpose the probe 14A is primarily formed of a light pipe core 48 of light-transmissive material, the detector 44 scintillation crystal being partially embedded in or otherwise optically coupled to the light pipe core 48 near the end of the core which is remote from the X-ray tube. To prevent ambient external light from affecting the optical X-ray count signals, a coating 49 of opaque material encloses all surfaces of the core 48 and of the X-ray detector 44 which would otherwise be exposed to ambient light. To reduce spurious X-ray count signals from radiation arriving at detector 44 from directions other than that of the collimator 29A, an additional inner lining 49 of lead or other highly radiation-absorbent material may enclose the end portion of the core 48 in the region of detector 44 except for the surface of the detector which faces the X-ray tube.

Probe 14A has a base end 51A releasably securable in any selected one of a series of attachment means 52A, 52B, 52C and 52D situated at different positions on the X-ray tube. As best seen by referring to FIGS. 1 and 2 in conjunction, attachment means 52A in this example is situated at one side of the collimator-receiving opening 28 at the mid-plane of the X-ray tube while a second essentially similar attachment means 52B is provided at the same plane on the opposite side of the collimator-receiving opening. Another attachment means 52C is located below the center of the collimator-receiving opening 28 while still another such attachment means 52D is situated above the center of the opening.

Attachment means 52A may include a cylindrical passage 53 penetrating for a distance into the face of housing 27 and shaped to receive base portion 51A of probe 14A. In order to assure that the probe enters the passage 53 only in an orientation which situates the X-ray detector 44 at the central axis of the X-ray tube, a linear rib or key 54 is formed on base portion 51A of the probe and is received in a conforming axially extending slot 56 in the wall of passage 53. To assure that the probe is firmly and fully seated in the attachment means with the X-ray detector 44 being situated at the point of convergence of radiation transmitted through collimator 59, detent means may be provided which in this example consist of a plunger 56 axially slidable in a passage 57 at right angles to passage 53 and having a spherical end surface suitable for engaging a conforming spherical cavity in the side wall of the base portion 51A of the probe 14A. Plunger 56 is biased towards passage 53 by a compression spring 58 and snaps into detenting position when the probe has been fully inserted while enabling easy removal of the probe when it is to be replaced with a probe of different configuration or when it is to be shifted to a different one of the attachment means 52.

In order to retract the plunger 56 as the probe 14A is being inserted in passage 53 and to provide for efficient coupling of optical signals to photomultiplier tube 46, the end 59 of the base portion 51A of the probe 14A is a projecting end of the light pipe core 48 having a conical configuration.

Each of the other attachment means 52B, 52C and 52D may have a similar construction except insofar as each such attachment means has a different angular orientation with the keyway slots 56 of each attachment means always being adjacent the collimator-receiving opening 28 and the detent means always being on the outward side.

To transmit X-ray count data optical signals from end 59 of probe 14A to the photosensitive surface of photomultiplier tube 46, a light pipe 61 is disposed within housing 27 and has a broad base portion 62 disposed against the photosensitive surface of the photo tube 46. Forward from base portion 62, the light pipe 61 divides into four arms 63A, 63B, 63C and 63D. Arm 63A has a forward end extending into the inner end of passage 53 of attachment means 52A and has a conical indentation receiving the pointed end 59 of the base 51A of probe 14A. To facilitate the transmission of optical signals across the boundary, the juncture between end 59 of the probe and the forward end of arm 63A of light pipe 61 may be coated with silicone grease or other known materials suitable for such purpose. The other arms 63B, 63C and 63D of the light pipe 61 extend to the other attachment means 52B, 52C and 52D respectively in an essentially similar manner.

To prevent external light from entering the passages 53 of the ones of the attachment means 52 which are not coupled to probe 14A during an operation of the system, opaque closure plugs 64 are inserted in the passages 53 of such attachment means and are disengageably retained therein by the same detent plungers 56B which otherwise engage a probe.

The probe 14A depicted in FIGS. 1 and 2 is designed to facilitate the obtaining of pantomographic images embracing a sizable portion of a dental arch of a subject 12. Such images are usually a panoramic image of approximately one-half of the dental arch. For such purposes, it is usually preferable to locate the X-ray detector 44 in the general vicinity of the patient's third molar tooth at the opposite side of the dental arch. To effect this detector disposition with a minimum of discomfort to the patient this particular probe 14A has an essentially quarter circular configuration between the linear base portion 51A and the immediate region of the detector 44 so that it curves around the front of the patient's face and extends a small distance into the opposite side of the mouth.

In order to obtain a complementary pantomographic image of the other side of the dental arch of the subject 12, closure 64 is removed from attachment means 56B and the probe 14A is removed from attachment means 52A. The probe is then rotated and inserted into attachment means 52B, and the closure 64 is then inserted into attachment means 52A. The probe 14A then extends from the opposite side of the face of the X-ray tube 13 as depicted by dashed lines 14A' in FIG. 1, the X-ray detector 44 again being situated at the same centered position as before. The X-ray tube 13, including the probe 14A, may then be rotated around to the opposite side of the patient or alternately the patient may be turned to locate the detector 44 in an essentially similar manner but at the other rear molar 65L of the dental arch.

Basically, the ability of a scanning X-ray system 11 of this general form to produce a radiographic image of a subject is not dependent on the presence of a collimator 29A since only X-rays which are directed towards the minute detector 44 can contribute to the image. The primary function of the collimator 29A is to minimize radiation dosage of the subject. In addition, the collimator acts to enhance contrast in the image by reducing spurious counts at detector 44 from scattered radiation, X-ray fluorescence and the like. As a practical matter, the collimator 29A may detract somewhat from definition in the image as compared with a similar scanning X-ray system not having a collimator but the magnitude of this effect can easily be kept within acceptable limits and may be made insignificant since any reduction of definition caused by the collimator may be made to be less than the inherent definition limitations of the image display device 17. As the matter of reducing patient radiation dosage is generally a more critical one, it is usually desirable in dental or medical usages to operate system 11 with the following 29A in place.

The collimator 29A of this invention is of a specialized construction which provides for a high degree of reduction of patient radiation exposure while minimizing any consequent loss of image definition. In particular, the collimator 29A includes a collimation element 67 formed of lead glass or other radiation absorbent material having similar properties. Collimation element 67 is formed with a large number of spaced-apart radiation transmissive passages 68, of very small cross-sectional area, for transmitting X-rays which originate at target surface 26 towards the detector 44. The passages 68 are aligned in directions which are convergent at the X-ray detector 44. In other words, each of the passages 68 extends along a separate radius of a hypothetical sphere having the apex end of detector 44 as a center.

Referring now to FIG. 3, the impact of the electron beam 23 on target anode plate 26 causes X-rays 69 to be emitted in all directions from the point of impact. The effect of the collimator 29A is to absorb those of the X-rays 69 which are emitted in the general direction of the patient but which are not traveling precisely towards the detector 44 and therefore cannot contribute useful information to the desired image. The collimator has a similar effect on secondary X-rays which may be produced by interaction of a primary X-ray 69 with material behind or within the collimator.

As may be seen by reference to FIG. 4, which is a cross section of the collimator 29A taken at right angles to the plane of FIG. 3, the radiation transmissive passages 68 are convergent toward detector 44 when viewed in an orthogonal plane as well as in the plane of FIGS. 1 and 3 and thus the effect of the collimator is to intercept X-rays 69 which are directed towards the subject 12 other than the particular X-rays 69' which are directed exactly towards detector 44, regardless of the angular direction in which the unusable X-rays 69 deviate from a line extending towards the detector.

Referring again to FIG. 1, the X-rays produced at target anode plate 24 by impact of the electron beam 23 include X-rays of various different energies and the lowest energy component of the X-ray spectrum is of little or minimal value insofar as the production of the desired image is concerned. To avoid unnecessary exposure of the patient to these low-energy X-rays, one or more absorbent filtering means formed of a low-atomic-number material, such as aluminum for example, may be situated between the target anode plate 26 and the patient. In this example a first such filter layer 71, which may typically be two or three millimeters of aluminum or equivalent radiation absorber, is disposed against the forward surface of the target anode plate. Additional suppression of low-energy X-rays may be provided for by disposing another layer 72 of filter material on the surface of collimator element 67 which is closest to the target anode plate and by providing still another layer of such material 73 on the outer surface of the collimator element. The outer layer 73 of filter material has the further beneficial effect of absorbing scattered X-rays arising from scattering effects within the collimator 29A itself. For similar reasons, the radiation transmissive passages 68 may be filled with a material such as aluminum or any of various suitable plastics which absorb very low-energy X-rays in order to further reduce radiation dosage from X-ray scattering within the collimator. Thus it should be understood that the radiation-transmissive passages 68 are not necessarily unobstructed open passages nor are they necessarily transmissive to all forms of X-rays. The term radiation-transmissive passage is herein used to define a zone through the collimator which is transmissive to X-rays of a desired energy but not necessarily transmissive to other things.

A collimator element 67 having the physical characteristics described above may be manufactured by very precise drilling of the passages 68 through a lead glass element and if formed in this manner, laser beam drilling techniques may be preferred in order to enable the providing of a very large number of closely spaced passages 68 of a very minute cross-sectional area. As a practical matter it is preferable to form the collimator element 67 by fiber optical techniques similar to those heretofore used for manufacturing microchannel plates as used for example in night-vision devices and image-intensifiers. In one such technique, for example, the element 67 is initially formed by disposing a large number of tubular lead glass rods in parallel relationship with the passages through the rods being initially filled with a water- or acid-soluble core material. The array of glass rods is then fused by heating and is then drawn, in which process interstices between the adjacent glass rods are eliminated and cross-sectional size is reduced. The fused array, known as a boule, is then cut transversely to produce an element of the desired thickness. The resulting fused array is then etched to remove the soluble core material from the passages and the faces are polished to form the desired microchannel plate. Elements can be produced by these techniques in which the passages 68 are typically about 25 microns in diameter and have a center-to-center spacing of about 37 microns. After processing to the extent described above, the collimating element has passages 68 which are parallel rather than convergent. To produce the desired convergence, a sagging process may be used in which the microchannel plate is disposed on a sphere having a center at the point towards which the passages are to converge. The element is then heated to a temperature where sagging occurs either as a result of the weight of the mass of the microchannel plate or if necessary with the aid of externally applied pressure. This sagging causes the plate to conform to the surface of the sphere which deformation has the effect of causing the initially parallel passages 68 to now be convergent at the center of curvature of the sphere.

As will hereinafter be discussed in more detail, the primary effect of this sagging is to produce the desired convergence of the radiation-transmissive passages 68. The spherical curvature of the collimator element 67 as a whole as depicted in FIG. 1 is also produced by the sagging operation and may have an advantage in many cases in that it enables closer fitting of the X-ray source against curved exterior portions of the patient's anatomy such as the curvature in the jaw region. However, in other instances the collimator element 67 need not have an overall curvature but can be planar provided that the internal passages 68 have the desired convergence, an example of such a flat collimator being hereinafter described. If the collimator is to be flat, it may be produced by a somewhat different process which does not involve the sagging step. In particular, a fused array of hollow lead glass capillary tubing may be heated and drawn into the form of a long cone both to reduce passage size and to produce the desired convergence of all passages towards a single point. A desired flat section of the cone may then be produced by transverse cuts, with the resulting flat end surfaces being polished to produce the finished collimator element. This technique is capable of producing passages 68 down to around 200 microns in diameter without difficulty although with care still smaller passages may be produced.

In instances where it will not be necessary to change the focal length of the X-ray tube, defined as the distance between the detector 44 and the target anode plate 24, the collimator 29A may simply be permanently mounted in position at the face of the X-ray tube. The embodiment of FIG. 1 utilizes a releasable collimator 29A so that the collimator may be removed and replaced with another collimator in which the passages 68 converge at a point further out from or closer to the target anode plate depending on whether focal length is to be increased or decreased. For this purpose the collimator element 67 is disposed in a rectangular frame 74 which fits into the collimator-receiving opening 28 at the face of the tube and which is disengageably retained therein by threaded screws 76 and which is preferably formed of radiation-absorbent material. As best seen in FIG. 2, screws 76 extend into the forward side portions of housing 27 and enter a short distance into appropriately located bores in the side of the collimator frame 74. Thus by disengaging the screws 76, the collimator 29A may be removed from opening 28 and another collimator of different focal length may be inserted and may be held in place by reengaging the screws. Screws 76 may be replaced by more elaborate but more quickly operated latching means in instances where frequent changes of focal length are contemplated.

Referring again to FIG. 1, a pantomographic image of the left side of the dental arch of a subject 12 will be produced on screen 18 of X-Y display device 17 by coupling the output of an X-sweep frequency generator or oscillator 77 to both the X-sweep terminal 78 of beam deflector 31 and to the X-sweep terminal 79 of the display 17. The output of a Y-sweep frequency generator 81, which produces a repetitive sweep wave form of substantially lower frequency than that of the X-sweep frequency generator 77, is coupled to the Y-sweep signal terminal 82 of the beam deflector 31 and also to the Y-sweep terminal 83 of the display device 17. Accordingly, the electron beam 23 is caused to repetitively sweep through a raster pattern on target anode plate 24 and the electron beam sweep of the display device 17 is coordinated with that of the source. Circuits for this purpose will hereinafter be described in more detail.

The X-ray count signals produced at detector 44 vary in number in the course of this scanning action in accordance with variations of the radiation-transmissiveness or radiolucence of the particular portion of the patient's anatomy which is being intercepted by X-rays 69' at each successive time in the course of the scanning action. The count signals, which are initially optical signals, are transmitted by light pipe core 48 of probe 14A and then by the internal light pipe 42 of the X-ray tube to photomultiplier tube 46 where the count signal data is translated into an electrical voltage signal. The output signal terminal 84 of photomultiplier tube 46 is coupled to the Z or intensity signal terminal 86 of display device 17 through a video type of amplifier 87. Thus successive points in the visible image at the screen 18 of device 17 have a degree of illumination intensity determined by the radiation transmissiveness at the corresponding points in the region of the patient's anatomy which is being scanned and the image at screen 18 constitutes the desired radiographic image. If each complete scanning raster is completed within the period of eye persistence of the human biovisual system, the image may be viewed directly at screen 18. The image may also be viewed in that manner, without regard to such scanning time limitation, if a long persistence cathode ray tube screen 18 is used and preferably one of the adjustable persistence type. To provide a permanent record or to provide the viewable image itself where a relatively long scanning time and short persistence screen 18 prevent direct viewing, a camera 18' may be used to photograph the screen with the exposure time being equal to that required for at least one complete scanning raster.

Suitable additional components for the above described control circuit 16, by which various electronic image enhancement techniques may be utilized if desired and by which radiographic image data may be stored on magnetic tape or the like instead of utilizing the cumbersome conventional film storage, are described in applicant's prior U.S. Pat. No. 3,949,229 and may be embodied in the present system if desired. The electrical control circuit 16 of this example will hereinafter be described in more detail in connection with certain additional provisions which may be employed in the circuit to alleviate forms of optical distortion in the image which can otherwise be present.

Certain structural arrangements have been mentioned above for the purpose of selectively changing the focal length of the system. A focal length adjustment may be needed where a single instrument is to be used for the production of both wide-angle panoramic pantomographic images and also periapical dental radiographs or other images in which a smaller portion of the subject is to be imaged at a larger magnification. This is accomplished by replacing the probe 14A with another probe which locates the detector 44 further out from the target anode plate 24 when focal length is to be increased or which locates the detector closer to the target anode plate when focal length is to be decreased. When the location of the detector 44 is changed in this manner, collimator 29A must also be replaced with another collimator having radiation transparent passages 68 convergent towards the new location of the detector 44. Still another adjustment may also be made in conjunction with such a change of probe and collimator. In particular, if the region within the X-ray tube 10 where the electron beam 23 is being deflected from the central axis of the tube is spaced from the target anode plate 24 a distance substantially different from the spacing of the detector 44 from the target anode plate a distortion of the image can occur. Although such distortion can be tolerated in many instances, it may be reduced or eliminated if in conjunction with the above-described change of probe and collimator to select a different focal length, the axial position of the deflector 31 is also shifted by the previously described means so that the electron beam deflection region and the detector 44 remain substantially equidistant from, or in constant distance ratio to, the target anode plate surface 26.

FIG. 5 depicts the forward portion of the X-ray tube 13 after adjustments have been made as discussed above in order to increase the focal length. Thus in FIG. 5, the original probe has been replaced with a new probe 14B which may have an internal construction essentially similar to that of the probe described above except that it is of greater length to position the detector 44B further out from the face of the tube. The curvature of the probe 14B may also be modified as necessary to maximize patient comfort. Similarly, the original collimator has been replaced with a second collimator 29B in which the radiation-transmissive passages 68B have a different angular orientation in order to be convergent at the new, more distant, location of the detector 44B. It may be observed that collimator 29B also differs from that depicted in FIG. 1 by being of the flat configuration previously described.

The forms of probe 14 described in connection with FIGS. 1 to 5 are primarily designed for production of pantomographic dental X-rays and have been shown and described as being mounted at one lateral side or the other of the face of the X-ray tube. For other purposes, such as the making of periapical dental X-rays, the probe may have a considerably different configuration and may be attached to the X-ray tube at a different location. FIG. 6 depicts the forward portion of the X-ray tube 13 as adjusted to provide for the making of periapical X-ray images of individual teeth or of a small number of individual teeth of the lower jaw of the patient. In particular, a modified probe 14C is mounted on the face of the X-ray tube at the particular attachment means 52B which is situated above the central axis of the tube. The modified probe 14C has a different configuration from the previously described probe and extends directly forward from the face of the tube and has a slight downward curvature towards the remote or distal end of the probe. In this example this situates the detector 44C at a differing distance from the face of the tube than in the case of the other probe and therefore a different collimator 29C is utilized which has a correspondingly changed focal length as hereinbefore described.

The same modified probe 14C may then be used to make periapical X-rays of teeth of the upper jaw by removing the probe from attachment means 52D and remounting it in the lower attachment means 52C below the collimator 29C as shown by dashed lines 14C' in FIG. 6. Use of the apparatus of FIG. 6 to make a periapical X-ray image of the upper incisor teeth of a patient, with the probe at dashed line position 14C' is depicted in FIG. 7. In particular, the X-ray tube 13 may be positioned directly in front of the patient's upper jaw with the probe 14C' extending into the patient's mouth and slightly upwardly to locate the detector 44C of the probe directly behind the upper front incisor teeth of the subject 12.

In order to support the X-ray tube 13 including probe 14C', a mounting bracket 88 may be secured to housing 27 at the underside of the housing in this instance for connection to suitable support means 89. The support means 89 in this example is a semi-rigid tubular gooseneck of the form which can be bent to different configurations by applying sizable force but which is otherwise sufficiently rigid to support the X-ray tube 13 in a selected position and orientation. In instances where the weight of the X-ray tube 13 or other causes require a non-bendable support, scissors brackets or the like of the known forms used to support more conventional dental X-ray tubes may be used. Support means 89 may, if desired, attach to a housing 91 which contains electrical control circuit components of the system in which case conductors for coupling the electrical components of the tube with the rest of the circuit may be situated within the support tube 89.

The examples of the invention described above have utilized replaceable probes having lengths and configurations designed to facilitate the making of certain specific forms of dental radiograph. It should be understood that other probes 14 may be provided with different lengths and configurations suitable for making other types of radiograph either with invivo subjects or in connection with X-ray inspection of inanimate objects such as metallurgical castings for example. FIG. 8, for example, illustrates the forward portion of the X-ray tube 13 supporting still another probe 14D which is designed for facilitating the making of a medical X-ray image of the central region of a patient's head and showing, among other anatomical features, the bony structure of the ear. For this purpose, the probe 14B may be mounted in one of the side attachment means at the face of the tube, attachment means 52B in this case. Probe 14D is of greater length than those previously depicted and described and is shaped to curve around the head of the patient and to enter a small distance into the ear canal at the side of the patient's head opposite from the face of the X-ray tube. As will be apparent, a variety of other probe configurations may be utilized to locate the detector at appropriate positions either at the opposite side of a patient from the X-ray source or within any of various body cavities and openings into which probes may be inserted. Similarly, probes having still other configurations may be provided to locate the detector within cavities of manufactured industrial parts, such as castings, for example, which are to be inspected by X-ray imaging.

Reference has been made to the fact that the basic electrical control system insofar as hereinbefore described may under certain circumstances result in the presence of forms of optical distortion in the visible image at the display device 17. Distortions may be tolerated in the image, at least for many purposes provided that the dentist, doctor or other interpreter of the image is aware of the distortions and makes appropriate allowances in interpreting the data. However, it is obviously preferable to reduce or eliminate such distortions to the extent possible in order to simplify the task of image-interpretation. The present invention further provides control circuit components for this purpose.

Components for eliminating a distortion which could otherwise arise from changing the relative spacing of the detector and the tube electron beam deflection region from the target anode plate have already been described. Several other forms of image distortion or image degradation can occur unless corrections are provided for. These include both geometrical distortions arising from variations of degree of magnification at different areas of the image and image intensity variations arising from unwanted variations of the amount of radiation which reaches the subject or the detector at different times or at different areas of the scanning raster.

Considering variable magnification effects first, it should be appreciated that convenient adjustment of the degree of magnification of the subject in the image is one of the advantages of a scanning X-ray system of this general type. This can be done in either of two ways. A first method is to increase or decrease the size of the scanning raster at the visual display device 17 relative to the scanning raster size at the X-ray tube 13. The other method is to change the position of the subject relative to the target anode plate 24 and detector 44. If the subject is positioned relatively close to the detector 44 it is highly magnified in the image although the field of view is reduced. Conversely, if the subject is repositioned closer to the target anode plate 24 and further from the detector 44, magnification is decreased but a wider-angle view is obtained.

The first method of magnification control can readily be effected simply by adjusting the beam deflection controls of either the X-ray tube 13 of the visual display device 17 or both. The second method is accomplished by simply moving the X-ray tube 13 and probe 14 relative to the subject or vice versa.

The problem of variable magnification at different regions of the image arises in part from the same factors which underlie the second method of magnification adjustment described above. By referring to FIG. 9, it is readily apparent that the several teeth of the dental arch 12 which are being displayed in the image have different relative positions between the target anode plate 24 and the detector 44. Teeth near the center of the image area are relatively close to the target anode plate 24 and relatively distant from the detector 44 as compared with the teeth nearer the sides of the image area. Thus, in accordance with the factors discussed above, the teeth will exhibit different degrees of magnification in the image in the absence of a correction.

A second factor which can cause variable magnification at different areas of the image arise from the fact that if the rate of scanning of the electron beam along the target anode plate 24 is uniform, then the effective rate of scanning along the subject to be imaged may not be uniform. Referring again to FIG. 9, the teeth of the dental arch 12 to be imaged in this example are situated approximately along a circular arc A having a radius R and having a center of curvature D at the detector 44. If the electron beam of X-ray tube 13 is scanned in the X-direction, that is in the plane of FIG. 9, at a uniform speed, the effective scanning rate along arc A is variable. Effective scanning rate is slowest along the central portions of arc A which are closest to being parallel to the target anode plate 24 but progressively increases toward the end portions of arc A which increasingly curve away from the plane of the target anode plate. In the absence of correction, the practical effect is that the central teeth occupy a disproportionately large amount of the image in the X or lateral direction or, in other words, tend to be more greatly magnified in the X direction than are the teeth nearer the sides of the image.

Both of the variable magnification effects described above may be reduced or substantially eliminated by delinearizing the scanning sweep speeds in both the X and the Y directions in either the X-ray tube 13 or the visual display device 17 in order to compensate for the effects described above. It is preferable to delinearize the scanning action of the X-ray tube 13 for this purpose, and electrical circuits for this purpose will be hereinafter described. In order to best understand the operation of such circuits, a more mathematical analysis of the above-described effects is required.

In FIG. 9, point 0 designates the center of the target anode plate 24 which is the point of impact of the undeflected electron beam along the axis of the tube and defines the origin point of the coordinate system for the following equations. Point P represents an arbitrarily chosen point of electron beam impact on the target anode plate in the course of a scanning raster. The letter D designates the position of the detector 44 at the center of curvature of arc A along which the teeth to be imaged are situated while R is the radius of the arc. C designates the fixed distance of arc A from point O along the central ray path O-D while V is a variable representing the distance of arc A from the momentary electron beam impact point P. X is a variable representing the displacement of point P from point O in the X-scan direction and $\theta$ is a variable representing the angle formed by ray lines O-D and P-D. S is the coordinate distance of ray line P-D from ray line O-D measured along arc A.

From basic trigonometric relationships, it may be seen that:

$$X = (R+C) \tan \theta \tag{1}$$

and $$S = R\theta \tag{2}$$

From (1) and (2), it follows that there is a non-linear relationship between S and X since S varies linearly with $\theta$ while X varies as the tangent of $\theta$. Thus if the electron beam sweep rates of both the X-ray tube 13 and the visual display device 17 are constant, image distortion occurs wherein teeth closer to the central ray path O-D are more greatly magnified than teeth which are further away from path O-D. In order to remove this particular form of distortion, $\theta$, rather than X, is caused to vary in a linear manner in the course of each X-direction scan. This is accomplished by causing the electron beam sweep rate, in the X-direction, to vary as a function of the tangent of $\theta$, suitable electrical circuit means for this purpose being hereinafter described. A similar correction may be applied to correct for curvatures in the orthogonal or Y-direction where the configuration of the subject makes it advisable.

Considering now suitable corrections for variable magnification effects in the Y-direction, that is at right angles to the plane of FIG. 9, for a subject having the configuration of dental arch 12 it should be assumed, to avoid unnecessary complication of the present analysis, that all of the teeth lying along arc A have the same vertical height in the Y-direction. FIG. 10 is a diagrammatic section view taken along line X-X of FIG. 9 or in other words along a vertical plane containing the central ray path O-D. The tooth T1 which that plane intercepts requires a Y-direction sweep distance of $Y_o$ in order to be fully imaged and is magnified by the factor $(R+C)/R$ for the reasons hereinbefore discussed. FIG. 11 is a diagrammatic section view taken along line XI—XI of FIG. 9 or in other words along a vertical plane containing the ray path P-D. The different tooth T2 which the plane of FIG. 11 intercepts requires a Y-direction sweep distance of $Y_p$ in order to be fully imaged and is magnified by the factor $(V+R)/(C+R)$ relative to the magnification of tooth T1. Thus while the teeth T1 and T2 of FIGS. 10 and 11 respectively are actually of the same height, tooth T2 is more greatly magnified in the image than is tooth T1. By analyzing this effect for a series of additional vertical planes, it may be seen, referring back to FIG. 9, that objects of constant height such as the teeth are assumed to be in this case and which lie along arc A become increasingly more magnified in the image as S increases in either direction from the central ray path O-D. This effect may be reduced or eliminated by delinearizing the Y-direction electron beam sweep rate in the X-ray tube 13. The Y-sweep rate correction needed for this purpose is derived as follows:

Referring to FIGS. 10 and 11, it may be seen that:

$$Y_p/Y_o = (V+R/C+R) \tag{3}$$

From FIG. 9, it may be seen that:

$$(V+R/C+R) = \sec\theta \tag{4}$$

Combining (3) and (4) gives:

$$Y_p/Y_o = \sec\theta \tag{5}$$

The objective of the correction is to cause all teeth in the image to exhibit the same height $Y_o$ since as postulated for the present analysis, that is the actual fact. Mathematically this may be derived as follows:

The displacement in Y that passes through the origin 0 varies with time:

$$Y_{ot} = F(t) \tag{6}$$

In this example, F(t) is a triangular wave function owing to the lack of significant curvature of the teeth in the vertical direction.

Combining (5) and (6) gives:

$$Y_p = F(t) \sec\theta \tag{7}$$

Thus the Y-direction sweep rate of the electron beam in the X-ray tube 13 should be delinearized and caused to vary as a secant function of $\theta$, circuit means for this purpose being hereinafter described.

Use of the secant function for this purpose results from the disposition of the teeth along an arc A having a constant radius of curvature R. If the object or series of objects to be imaged lie along a path having some other configuration wherein the radius of curvature is not constant, but instead varies as a function of $\theta$, then a more complicated function than the secant function must be generated by essentially similar trigonometric analysis.

Considering now techniques for correcting those forms of image degradation which are not geometrical in nature but instead cause undesirable variations in intensity or contrast in different regions of the image, reference should again be made to FIG. 9. Like many other subjects, the teeth which are to be imaged in this example are of different thickness along the X-ray paths from the target anode plate 24 to detector 44. Thus the X-ray energy level best suited for producing a clear image of one tooth may not be the value best suited for imaging others of the teeth which have a different radiolucence. In the example of FIG. 9, the teeth tend to increase in thickness and therefore in radioopacity from the front of the patient's dental arch 12 towards the back or, in the depicted geometry, in the direction of increasing $\theta$. In other words, the X-ray absorbency of the subject to be imaged is lowest at the extreme minus $\theta$ portion of the X-direction scan and tends to increase as the angle $\theta$ approaches its maximum positive value.

Clarity of the image may be enhanced by changing the energy of the electron beam within the X-ray tube 13 in the course of the scanning action in a programmed manner which compensates for the variations of radiolucence of different regions of the subject which have been described above, circuit means for this purpose being hereinafter described. In the example of FIG. 9, this may take the form of progressively increasing electron beam energy, in the course of each X-scan, as a function of $\theta$. If a more precise compensation is desired, the energy change in the course of each scan need not be a continuous gradual rise but may consist of a series of stepped increases or decreases each determined by the radiolucence of the particular tooth or portion of a tooth being imaged at successive stages in the scan. Alternately, an acceptable degree of compensation may often be achieved by simply changing electron beam energy level once in the course of each scan at the stage where the scan passes between the relatively thick back or molar teeth and the more radiation-transparent anterior teeth.

Essentially similar programming of beam energy at different regions of the scanning raster may be used where the subject is something other than the teeth of a dental patient but which also exhibits pronounced differences of thickness and/or of radiation absorbency at different regions. While the foregoing discussion of varying X-ray energy has dealt with variations in the X-direction, similar steps may be taken in conjunction with the scanning action in the orthogonal or Y-direction if the characteristics of the subject make it desirable. Thus, with reference to FIG. 10, electron beam energy may be varied in a continuous or stepped manner or in a combination thereof as a function of angle $\theta$ as determined by variations of radiolucence of the subject in the Y-direction.

To enhance image clarity, it may also be desirable to assure that the radiation flux intensity applied to the subject throughout the scanning action remains substantially constant aside from the deliberate variations to accommodate to variations of radiolucence as described immediately above. In the absence of corrections, non-uniform irradiation of the subject at different regions of the scanning raster may occur simply as a result of the fact that the X-rays originate at different points on the target anode plate 24 at different times in each scanning raster. Two different effects create such a non-uniformity. A first such effect is the attenuation of a radiation flux with distance in accordance with the well-known inverse square law. Referring again to FIG. 9, it may be seen that ray path P-D is longer than the central ray path O-D and in general the distance which X-rays must travel from the target anode plate 24 to detector 44 progressively increases from the center of the X-scan towards each extremity of such scan. This is also true of scanning action in the Y-direction. Owing to inverse square law attenuation this will cause count rate variations at the detector 44 even if a subject of uniform X-ray opacity is being imaged or if there is no X-ray absorber at all between the X-ray source and the detector. More specifically, as the electron beam moves away from the central point 0, there is a fall-off in X-ray count rate at detector 44 which varies as a function of the ratio: $(R+C)^2/r^2$, where r is the distance of the detector 44 from the momentary point of impact of the electron beam on target anode plate 24. This relationship does not take into account the second effect which causes an unwanted variation of X-ray count during the scanning action and which will now be discussed.

In particular, the target anode plate 24 at which X-rays originate has a finite thickness which is not evident in FIG. 9 but which may be seen by reference to FIG. 12 wherein such thickness, designated T, has been greatly exaggerated for clarity of illustration. An arbitrary point of electron impact on target anode plate 24 is identified by the letter E in FIG. 12 and its coordinates are shown as r, $\theta$ and $\theta$ with such coordinates and other symbols having the same meaning as in the previous figures and discussion except that it should be understood that r, the distance from the X-ray origin point to detector 44, includes the thickness T of the target anode plate.

X-rays originating at point O at the center of the scanning raster pass directly through the target anode plate 24 to reach the detector 44 and are attenuated to some specific degree because of abosrption by the target anode plate material. X-rays originating at an off-center point such as E must pass obliquely through the thickness T of the target anode plate and are therefore attenuated to a greater degree. The effective length of the X-ray path through the target anode plate, designated $T_r$, progressively increases towards the extremities of the scan in both the X and the Y directions. Thus a corresponding unwanted variation of X-ray count rate occurs at detector 44 unless a correction is provided.

Correction for both the inverse square law form of X-ray count variation and the variable effective target thickness form of X-ray count variation, may be realized by varying the electron beam current within the X-ray tube 13 during the scanning operations to adjust radiation flux in such a manner as to compensate for these effects. Considering now the electron beam current variation needed for this purpose, it has been previously pointed out that insofar as the inverse square law effect alone is concerned, X-ray count rate at the detector 44 varies as a function of the ratio $(R+C)^2/r^2$. When the variable absorption effect in the target anode plate effect is also taken into account the unwanted variation of X-ray count may be represented by the following relationship:

$$I/I_o = [(R+C)^2/r^2]e^{-\mu T_r} \tag{8}$$

where

I = X-ray flux to the detector from arbitrary point E,
$I_o$ = the minimally attenuated X-ray flux to the detector along the central ray path O-D,
$\mu$ = the linear absorption coefficient of the target anode plate material and wherein the other terms have the previously described meanings.

Referring to FIG. 12, it may be seen from trigonometric relationships that $$T_r = T \sec\theta \sec\phi \tag{9}$$

Since the objective is to cause a constant flux of radiation to be received at the detector, in the absence of a subject to be imaged, from all positions on the target anode plate, that is for all values of $Y_p$ and $\theta$, the right side of expression (8) must be multiplied by a correction factor K which will cause the left side of expression (8), that is $I/I_o$, to be a constant for all values of $Y_p$ and $\theta$. The correction factor K may be expressed as:

$$K = K(Y_p, \theta) = r^2 e^{\mu T_r} \tag{10}$$

For small amounts of X-ray attenuation, the following approximation is acceptably valid:

$$e^{\mu T_r} \approx (1 + \mu T_r) \tag{11}$$

combining expressions (10) and (11) gives:

$$K = r^2(1 + \mu T_r) \tag{12}$$

From FIG. 10, it may be seen that:

$$r_o^2 = Y_o^2 + (R+C)^2 \tag{13}$$

and $$\sec\phi = r_o/R + C \tag{14}$$

Therefore from (9) and (14) it may be seen that:

$$T_r = (r_o/R + C)(T \sec\theta) \tag{15}$$

From FIG. 9, 10 and 11, it may be seen that:

$$r^2 = r_o^2 \sec^2\theta \tag{16}$$

Substituting expressions (15) and (16) into (12) gives:

$$K = r_o^2 \sec^2\theta[1 + \mu T r_o \sec\theta/(R+C)] \tag{17}$$

which represents the variation of electron beam current in the course of each X-direction scan which is needed to compensate for the unwanted variation of X-ray count at detector 44 which has been previously described. Suitable circuit means for varying electron beam current in accordance with this relationship (17) will be hereinafter described.

The several different forms of potential optical distortion and image clarity degradation described above may be greatly reduced or eliminated by delinearizing the rate of the electron beam sweep in the X-ray tube 13 in both the X and Y directions and by modulating electron beam energy and current in accordance or in approximate accordance with the several mathematical functions which have also been described above. A suitable electrical control circuit for accomplishing each of these corrections is depicted in FIG. 13.

Referring now to FIG. 13, electron beam generating and controlling elements of the X-ray tube 13 include a cathode 101 which emits electrons upon being heated by a filament 102 in the conventional manner and which has a terminal 101' to which a high negative electrical potential is applied from a high-voltage supply 103 in order to produce an electrical field which accelerates the electrons towards the grounded target anode plate 24 of the X-ray tube. Maintaining the cathode 101 at a high voltage while grounding the anode 24 is the reverse of the conventional arrangement in X-ray tubes and offers the advantage that a dental or medical patient or an electrically conductive inanimate object may be placed very close to the face of the X-ray tube or even against the face of the X-ray tube without creating a risk of electrical shock. Where this is not a problem, the cathode may be grounded and a positive high voltage supply may be connected to the anode plate, if desired. The high voltage supply 103 is of the programmable form in which the magnitude of the output voltage delivered to cathode 101 is adjustable by varying an input voltage signal so that the electron beam energy may be modulated in the course of the scanning action as will hereinafter be discussed in more detail.

The electron gun 22 of X-ray tube 13 also has a control grid 105 with a terminal 105' to which a voltage may be applied for the purpose of modulating electron beam current as will also be discussed in more detail. The electron gun 22 may also have further elements such as a first anode 104 and ultor-focusing grid 106 which are not utilized in accomplishing the image corrections of the present invention but which are present for their conventional purposes. As previously described, the X-ray tube 13 also has an X-beam deflection coil 33X and a Y-beam deflection coil 33Y for controlling the point of impact of the electron beam on target anode plate 24, the coils respectively having an X-deflection signal terminal 78 and a Y-deflection signal terminal 82.

The control circuit is further provided with a regulated DC power supply 107 having a first output terminal B+ at which a constant positive voltage is provided for operating other components of the circuit and a second output terminal B-at which a constant negative voltage is provided for similar purposes. To avoid excessive complication in drawing, the power supply connections to most components of the circuit are not depicted where such connections may be of the conventional known form.

The X-sweep frequency generator 77 has an output terminal 77' connected to the X-sweep frequency terminal 79 of the visual display device 17 and may be of the known construction which generates a ramp signal output wave form of the type depicted at 77W which cyclically oscillates in a linear manner between a maximum negative voltage and a maximum positive voltage at a frequency corresponding to the desired X-sweep or scan frequency at both the X-ray tube 13 and the visual display device 17. Similarly, the Y-sweep frequency generator 81 has an output terminal 81' coupled to the Y-sweep frequency terminal of visual display device 17 and is of the known form that produces a ramp signal 81W similar in general form to that of the X-sweep frequency generator except insofar as it has a substantially lower frequency as determined by the number of horizontal scan lines which are desired in the scanning raster. The difference between the X and Y-sweep frequencies is normally much greater than appears from the wave forms 77W and 81W in FIG. 13, it being impractical to illustrate the actual difference because of space limitations in the drawings.

Optical X-ray count signals originating at the detector 44 are converted to electrical signals by photomultiplier tube 46 as previously described. The X-ray count signal output terminal 83 of photomultiplier tube 46 is coupled to the Z or intensity signal terminal 86 of the visual display device 17 through an adjustable gain amplifier 108 and then through one input of a differential amplifier 109. The other input of the differential amplifier 109 is connected to a selectable DC voltage source 111 which may consist of an adjustable contact 112 movable along a resistive element 113 having opposite ends connecting to the B+ and B− terminals of the DC power supply 107.

Adjustable gain amplifier 108 enables selective control of the voltage level of the intensity signal applied to the visual display device while the differential emplifier 109 and selectable voltage source 111 aids in suppressing detector noise by suppressing electrical pulses of less than a selected amplitude. This form of intensity signal channel is best adapted to instances where the average rate of X-ray counts at detector 44 is sufficiently low that individual counts are separated in time and can be distinguished and individually processed. In instances where a higher X-ray count is present such that X-ray count pulses pile up to produce a varying voltage level proportional to detected X-ray flux, rather than distinguishable pulses, an integrating form of Z signal channel may be utilized as described for example in prior U.S. Pat. No. 3,949,229.

The control circuit as described to this point can be utilized without further complication to produce an image at display device 17 if output terminal 77' of the X-sweep frequency generator is connected to X-deflection coil terminal 78 of the X-ray tube, output terminal 81' of the Y-sweep frequency generator is connected to terminal 82 of the X-ray tube and constant voltages are applied to the cathode terminal 101' and control grid terminal 105' of the X-ray tube but in that event each of the previously described forms of image distortion and image clarity degradation may be present. Such images may be useful under many circumstances particularly where the detector 44 is spaced a substantial distance away from the target anode plate 24 of the X-ray tube since the severity of several of these effects is an inverse function of the focal length of the system as determined by the degree of convergence of the various X-ray paths from the tube toward the detector. However, it is of course preferable that such distortions be reduced or eliminated, particularly where the detector 44 is situated relatively close to the X-ray tube 13 as is the case in certain of the dental usages hereinbefore described and in many other instances as well. Accordingly, compensation circuit means 114 are connected between the sweep frequency generators 77 and 81 and the X-ray tube 13 terminals in order to modify the X- and Y-sweep frequency wave forms and to modulate the electron beam energy and current in accordance with the several controlling mathematical relationships hereinbefore derived.

Compensation circuit means 114 relies primarily on a series of electronic function generators 116, 117, 118, 119 and 121 and multipliers 122, 123 and 124 which are depicted in block form in FIG. 13 inasmuch as such circuit components may be of known internal construction and are available commercially. In general, function generators of this kind produce an output voltage which varies, as a function of an input voltage, in accordance with a predetermined mathematical relationship. Function generator 116 for example is of the known form which produces an output voltage that varies as a tangent function of an input voltage while function generator 117 is of the form producing an output voltage that varies as a secant function of the input voltage.

Function generators 118 and 119 are of the form which produces an output voltage proportional to the square of the input voltage and function generator 121 produces an output voltage proportional to the square root of an input voltage. Multipliers 122, 123 and 124 are each of the known form that produce an output voltage proportional to the product of two voltages applied to two inputs of the multiplier. Function generators and multipliers of this general form are often used for example in analog computer circuits. While the design of such function generators is known, a suitable internal circuit for a representative one of the function generators 116 will be hereinafter described in order to facilitate an understanding of certain characteristics of the compensation circuit means 114 as a whole.

By referring back to the previously given mathematical expressions (1) and (2) and accompanying analysis, it may be seen that variable magnification effects in the X-scan direction may be compensated for by varying the X-sweep frequency signal as applied to terminal 78 of the X-ray tube 13 as a function of the tangent of $\theta$ rather than in the linear manner produced by the X-sweep frequency generator 77. For this purpose output terminal 77' of the X-sweep frequency generator may be coupled to the input of tangent function generator 116 through an adjustable gain amplifier 126 which enables adjustment of signal level to determine the length of the X-direction scan in the X-ray tube. Since the magnetic deflection system employed in the present example of the X-ray tube 13 is responsive to current through the X-deflection coil 33X, rather than to voltage as such as in the case of an electrostatic deflector, the output of tangent function generator 116 is coupled to X-ray tube terminal 78 through a current amplifier 127 and variable resistor 128. If an electrostatic deflection system is used in X-ray tube 13, a voltage amplifier may be substituted for current amplifier 127.

Although suitable internal circuits for a tangent function generator 116 are known, a specific example is depicted in FIG. 14 and will be briefly discussed in order to facilitate an understanding of certain properties of the modified wave forms which are applied to the X-ray tube control terminals.

Referring now to FIG. 14, the input X-sweep frequency wave form 77W applied to the tangent function generator 116 input terminal 116$i$ may be treated as consisting of a sequence of triangular electrical pulses of positive polarity alternated with similar but inverted pulses of negative polarity. The upper half of the circuit of FIG. 14 processes the positive portions of the input wave form 77W while the lower half of the circuit processes the negative portions of the input wave form. The input wave form 77W is applied to one input of a differential amplifier 129P which has a reference input connected to a selectable DC voltage source 131P which may be adjusted to cause amplifier 129P to suppress the negative portions of the incoming wave form while transmitting the positive portion on as a series of triangular positive pulses separated in time. A first diode 132P and variable resistor 133P are connected between amplifier 129P and a summing junction 134. A second diode 136P and variable resistor 137P are also connected between amplifier 129P and summing junction 134 except that in this instance the input of diode 136P connects to the output of amplifier 129P through the adjustable contact of a potentiometer 139P having a resistive element connected between the output of amplifier 129P and the negative power supply terminal B—. Similarly, a third diode 141P and variable resistor 142P are connected between the output of amplifier 129P and the summing junction 134 through the movable contact of another potentiometer 143P having a resistive element connected between the output of amplifier 129P and power supply terminal B—. Summing junction 134 is in turn coupled to the output terminal 116$o$ of the tangent function generator through an operational amplifier 144 and a resistor 146 connected in parallel with the operational amplifier.

FIG. 15A illustrates the wave form 77W of the X-sweep frequency signal applied to the input 116$i$ of the tangent function generator of FIG. 14. FIG. 15B illustrates the modified output wave form of the tangent function generator at output terminal 116$o$. In particular and with reference to the positive half only of the wave form of FIG. 15B, it may be seen that the output voltage rises in a nonlinear manner in a series of three voltage rise segments, a, b and c each of which taken individually is linear but which are of progressively increasing slope. The positive output voltage then decreases in a similar series of linear segments of progressively diminishing slope.

The circuit of FIG. 14 modifies the triangular input wave form in this manner since as the leading edge of the positive triangular pulse appears at the output of amplifier 129P, diode 132P conducts immediately to transmit a rising current to summing junction 134. Immediate conduction of diode 132P is provided for by adjusting selectable voltage source 131P to offset the forward bias of the diode with a base voltage output from amplifier 129P. This corresponds to the initial segment a of the wave form of FIG. 15B. Diodes 136P and 146P do not initially conduct because of the respectively more negative biases applied to the inputs of such diodes by potentiometers 139P and 143P respectively. As the input wave form continues to rise a point is reached where diode 130P begins to conduct and thereby increases the amount of current being applied to summing junction 134. Thus the current input to the summing junction now rises more sharply as represented by the wave form segment b of FIG. 15B. As the incoming wave form 77W rises still further, eventually diode 141P also begins to conduct thereby adding still a third increment to the current being delivered to summing junction 134 corresponding to the most steeply sloped segment c of the wave form of FIG. 15B. Operational amplifier 144 and resistor 146 convert this rising current at the summing junction 134 to a corresponding rising voltage output signal at output terminal 116$o$.

Subsequently, when the input voltage begins to decrease in a linear manner, a reverse sequence of operation occurs in which diode 141P stops conduction, then diode 136P later stops conduction and finally diode 132P stops conducting as the input wave form passes from the positive region to the negative region, to produce the non-linear descending portion of the positive part of the wave form of FIG. 15B.

The bottom half of the circuit of FIG. 14 is essentially similar to the top half except insofar as the diodes 132N, 136N and 131N are inverted relative to the counterpart diodes of the top half of the circuit and except insofar as the potentiometers 131N, 139N and 143N are connected to the B+ power supply terminal rather than the B— terminal as in the case of the counterpart potentiometers of the upper half of the circuit. Thus the lower half of the circuit modifies the negative portions of the incoming wave form in essentially the same manner that the upper half of the circuit modifies the positive portions of the incoming wave form and the two portions as modified as combined at summing junction 134 to produce the complete modified output wave form 77T at the output terminal 116o.

Referring again to FIG. 15B, it may be seen that this form of function generator does not produce the desired wave form in an idealized form free of discontinuities but instead approximates the desired wave form by a series of segments a, b and c which in themselves are linear. The remaining distortion in the image arising from this departure from an ideal modified sweep signal is sufficiently small that it does not present any practical problems in most cases. In instances where the remaining distortion needs to be further reduced, the circuit of FIG. 14 may be modified by adding additional stages of the diodes 132, 136, 141, variable resistors 133, 137, 142 and potentiometers 139 and 143 on both the positive upper side and the negative lower side of the circuit so that the output wave form as shown in FIG. 15B is modified by having a greater number of the linear segments a, b and c, each of shorter duration than in the present case, so that the desired idealized wave form is even more closely approached.

Considering now circuit means for correcting variable magnification effects in the Y-sweep direction, from the previously derived mathematical expression (7) and accompanying discussion, it should be recalled that the Y-sweep frequency signal 81W should be delinearized and caused to vary as a secant function of $\theta$. For this purpose, with reference again to FIG. 13, output 81' of the Y-sweep frequency generator is coupled to one input of multiplier 122. Output 77' of the X-sweep frequency generator is coupled to the input of function generator 117 through an adjustable gain amplifier 147. Function generator 117 produces an output wave form representing the secant function of $\theta$ and such output is transmitted to the other input of multiplier 122 through another adjustable gain amplifier 148. Thus as shown in FIG. 15C the output of multiplier 122 is a voltage wave form 122W corresponding to the linear Y-sweep frequency generator output signal 81W as delinearized to vary as a secant function of angle $\theta$ during each successive X-direction scan. As the output of the multiplier 122 is typically a low current voltage signal whereas the magnetic Y-deflection coil of the X-ray tube requires a relatively high current, the output of multiplier 122 is coupled to the Y-deflection signal terminal 82 of the X-ray tube through an adjustable gain amplifier 149 and a current amplifier 151 and variable resistor 152.

Considering now suitable circuit means for programming in changes of electron beam energy within the X-ray tube 13 in the course of each X-direction scan in order to compensate for variations of radiolucence of the subject as previously described, still another function generator 153 may have an input connected to the X-sweep frequency output terminal 77' through an adjustable gain amplifier 154 and has an output connected to the voltage control signal terminal 103' of programmable high voltage supply 103 through another adjustable gain amplifier 156. If the variation of X-ray energy in the course of the X-scan is always to be the same for all usages of the X-ray tube 13, then the function generator 153 may be of the form which produces some single predetermined modification of the input signal which corresponds to the desired change of beam energy in the course of the scanning action. For example, if the X-ray tube is always to be used to produce a pantomographic dental X-ray image under the conditions depicted in FIG. 1, wherein the teeth to be imaged are of more or less progressively increasing thickness from the left side of the image to the right, then, referring back to FIG. 13, the function generator 153 may be of the fixed form which simply produces a gradual relative rise of the output signal as compared to the input signal in order to cause the programmable high voltage supply 103 to progressively increase electron beam energy during the course of each X-scan line of the X-ray tube 13. Preferably and as in this example, function generator 153 is of the form which enables selection of any of a variety of functions in order to readily accommodate to different usages of the X-ray tube 13 and to subjects which may have differing patterns of varying radiolucence in the X-direction. The function generator circuit of FIG. 14, for example, offers considerable latitude for selection of different output waveforms by selected adjustments of the several variable resistances 133, 137, 142 and potentiometers 131, 139 and 143. Other forms of function generator enabling an even greater variety of predetermined wave form modulations are known to the art and may be utilized if desired.

Referring again to FIG. 13, the remaining components of the circuit means 114 compensate for the previously described unwanted variations of radiation flux level at the subject and at the detector arising from inverse square law effects and the variations of absorption of X-rays in the target anode plate 24 at different portions of the scanning action. The previously derived mathematical expression (17) is the controlling relationship in accordance with which the voltage applied to the control grid 105 of the X-ray tube must be varied in the course of the scanning action in order to vary electron beam current in such a manner as to compensate for these effects. As is immediately evident from expression (17), a considerably more complex correction function is involved than is the case with the other forms of correction described above.

In order to modulate control grid 105 voltage in accordance with mathematical expression (17), one input of multiplier 123 receives the output of secant $\theta$ function generator 117 through squaring function generator 118. Thus the one input of multiplier 123 receives a $\sec^2\theta$ signal. Output 81' of the Y-sweep frequency generator is coupled to the input of function generator 119, which is also a squaring module of the form that produces an output voltage proportional to the square of the input voltage. The output of squaring function generator 119 is connected to one input of a differential amplifier 157 having an output connected to the remaining input of multiplier 123. The other input of differential amplifier 157 is connected to a selectable voltage source 158 which may be of the form having a resistive element connected across the B+ and B− terminals of the power supply and having a movable element connected to the reference input of differential amplifier 157. Selectable voltage source 158 is adjusted to generate a voltage representing the constant $(R+C)^2$ term of mathematical expression (13). As the output of squaring function generator 119 is representative of the term $Y_o^2$ of that same mathematical expression and the two are summed by amplifier 157, the output of amplifier 157 in the $r_o^2$ term of the controlling mathematical expression (17). This $r_o^2$ signal voltage is multiplied by the $\sec^2\theta$ signal voltage from function generator 118 in multiplier 123. The output voltage from multiplier 123 is transmitted through a selectable gain amplifier 158 which is adjusted to scale the input signal by the constant $(\mu T/R + C)^2$ term of mathematical expression (17) and the output of amplifier 158 is then passed through the square root function generator 121 to produce a voltage signal representing the function $(\mu T/R + C)(r_o \sec\theta)$ at one input of multiplier 124. The other input of multiplier 124 receives the $r_o^2 \sec^2\theta$ voltage signal from the output of multiplier 123. Thus the output of multiplier 124 represents $(\mu T r_o^3 \sec^3\theta/(R+C))$ which is the second term in the sum given by mathematical expression (17). The correction factor K of expression (17) is then obtained by adding in the expression $r_o^2 \sec^2\theta$ which as previously described is available at the output of multiplier 123. For this purpose an adding amplifier 159 has one input connected to the output of multiplier 124 and has the other input connected to the output of multiplier 123. This results in an analog voltage appearing at the output of amplifier 159 which is representative of the desired correction factor K as defined in the previously given mathematical expression (17). The output of amplifier 159 is connected to the control grid terminal 105' of the X-ray tube in order to modulate electron beam current to provide the desired image correction.

As there is considerable variation in size and configuration of teeth or other anatomical structures among different individuals, adjustment of the several adjustable controls of the circuit of FIG. 13 to minimize image distortion may be facilitated by using a coarse, preferably flexible gauze material formed of X-ray opaque wires or the like. Such a gauze may be wrapped around the subject to be imaged and the scanning X-ray system may then be temporarily operated at a low power level while viewing the image of the gauze on the screen of the visual display device. The several controls of the distortion correction circuit may then readily be adjusted to bring the images of the wires of the gauze into parallelism in both the horizontal and vertical directions with the intervening open spaces being equalized. After linearization of the low-level image has been achieved, the gauze may be removed and the electron beam energy of the tube increased to the normal operating level for obtaining the desired radiograph.

While the circuit of FIG. 13 includes components for providing each of the several forms of image correction hereinbefore discussed, there are instances where at least some of the forms of distortion or image degradation are not significant enough to need correction in which case the corresponding corrective component portions of the circuit of FIG. 13 may be omitted. A notable example of this occurs when the X-ray tube and detector are used in a computed tomographic system such as that described in Applicant's hereinbefore-identified copending application Ser. No. 674,059. In some forms of computed tomographic system, the electron beam scanning raster at the X-ray tube may be limited to a single scan line in the X-direction. In such cases, the corrections herein described which involve the Y-direction are of course not needed.

With the exception of the correction for varying radiolucence of different regions of the subject being imaged, all of the several forms of potential optical distortion and image degradation discussed above derive from the essentially triangular, conical or pyramidal configuration of the scanned region as defined by the broad area of the target anode plate 24 as a base and the essentially point detector 44 as an apex. That is, all useful rays generated in the course of a complete scanning raster converge at the position of the detector 44 with the distance of the detector from the target anode plate along the shortest ray path, that is the central ray path O-D of FIG. 9, being defined as the focal length of the system.

The severity of these potential distortions and degradations diminishes as the focal length is increased, that is as the small detector 44 is moved further away from the target anode plate 24. This characteristic offers still another technique for reducing the degree of image distortion and degradation. In particular, and with reference to FIG. 16, this may be accomplished simply by increasing the focal length of the system or in other words by decreasing the degree of convergence of the ray paths from the X-ray tube 13E to the detector 44E. Under some circumstances, distortions and degradations may be reduced to a degree that little or none of the electronic signal compensations hereinbefore described are needed. Where conditions make it practical, the small X-ray detector of the previously described embodiments may simply be positioned further out from the face of the X-ray tube and a modified collimator may be used which has radiation-transmissive passages which are less convergent and which are directed at the more distant X-ray detector. However, in some usages, such an arrangement produces other adverse effects which outweigh the advantages of lessened distortion. For example, looking at FIG. 16, if a small detector were situated at the distant focal point 161 of such an arrangement, the image would include the particular teeth which are intended to be in the image but superimposed thereon would also be images of teeth or other anatomical structures at the other side of the dental patient's head and such images would tend to obscure the desired images of the particular teeth of interest. To avoid this problem, as well as others associated with a long focal length, the embodiment of FIG. 16 utilizes a modified detector 44E which differes from that of the previously described embodiments by being larger and by being situated between the tube 13E and the focal point 161 rather than at the focal point. The radiation-sensitive area of the detector 44E is preferably just large enough to intercept the X-rays traveling from the scanning raster at target anode plate 24E towards the focal point 161 since the configuration of the subject may limit detector size. In other words, a very large detector cannot be inserted into constricted spaces such as into the mouth of the dental patient of FIG. 16.

Because of these restrictions caused by geometry and detector-size limitations, the embodiment of FIG. 16 is particularly appropriate for periapical rather than panoramic imaging. The smaller field of view, which may be in some cases dictated by the restriction on detector 44E size, is characteristic of periapical radiography. For similar reasons, the embodiment of FIG. 16 may employ an X-ray source 13E of smaller size having a smaller scanning raster area. However, panoramic images may still be obtained by shifting the X-ray tube and detector and making a series of images. Thus the detector 44E and X-ray tube 13E may be shifted to the dashed-line positions 44E' and 13E' for example by rotation along an arc 163 having a rotational axis at the approximate center of curvature of the portion of the dental arch 12 being imaged. The X-ray tube 13E and detector 44E may also be translated in a direction parallel to that rotational axis so that both maxillary and mandibulary teeth or other cranial features may be imaged. If desired, all of the images taken from these different viewpoints may be displayed on a single screen for viewing or to make up a mosaic of views combining the entire dental arch on one picture. This may be done, for example, by mechanically coupling the visual display sweep centering control to such mechanical means as might be used for shifting the X-ray tube 13 and detector so that each image appears at a different location on the screen. In instances where the image on the face of the visual display device is to be photographed to provide a permanent radiograph, the camera shutter may be held open during the imaging process except during those periods when the X-ray tube 13E and detector 44E are in the process of being repositioned. By this means the entire dental arch 12 may be displayed on one radiographic photograph. The detector 44E may, if desired, be supported and positioned by a probe 14E similar to those previously described and other portions of the system of FIG. 16 may be similar to the corresponding parts of the previously described embodiments.

Systems which employ a sizable detector 44E are more subject to spurious X-ray counts from scattered radiation, secondary X-rays and the like than are systems using the minute detector of the previously described embodiments. This is itself a form of image degradation since such spurious counts fog the image and reduce contrast. Thus selection of a system similar to that of FIG. 16 as opposed to one of the earlier described embodiments is a matter of weighing the relative advantages and disadvantages of each with reference to the specific use conditions. However, image degradation from spurious counts may be considerably reduced in the FIG. 16 system by utilizing an additional collimator 164 which is situated between the subject and the detector. In the present instance the additional collimator 164 is secured directly against the detector 44E as this maximizes effectiveness, minimizes collimator size and facilitates positioning and support of the collimator. Secondary or scattered X-rays which are traveling in the general direction of the detector but at angles other than that of the X-rays from the primary collimator 29E are absorbed by the additional collimator 164 and thus do not produce erroneous signals in the detector. Under some circumstances, notably where the subject to be imaged is not a living organism for which radiation dosage should be minimized, the additional collimator 164 may be used without the primary collimator 29E. Either collimator alone is capable of limiting X-ray transmission from the tube to the detector to a single path at a given instant in order to enable the production of an image. However, where the subject is a living organism, the presence of a collimator between the subject and the X-ray tube is beneficial in that it suppresses X-rays which are not directed towards the subject along the particular path from which meaningful image data can be obtained.

While the operation of the system has been discussed primarily with reference to obtaining an instantaneous radiographic image at the screen of the visual display device 17 of FIG. 13, it should be understood that the electronic signals carrying the image data and which are transmitted to terminals 79, 83 and 86 in FIG. 13, may alternately or at the same time be stored on magnetic tape or by other means for later reproduction of an image. Any of the various image-enhancement techniques as employed, for example, in the processing of video signals in television systems or in computed tomography may also be utilized to enhance the image, to emphasize certain image characteristics or to create specialized image displays. Similarly, the image displayed at the screen 18 of visual display device 17 may be photographed to provide a permanent radiograph. Techniques for storing and processing signals from a scanning X-ray system of this general type in these ways are described in applicant's prior U.S. Pat. No. 3,949,229.

While the invention has been described with respect to certain specific embodiments, numerous modifications are possible and it is not intended to limit the invention except as defined in the following claims.

What is claimed is:

1. A method for alleviating image distortion in a scanning X-ray system wherein an electron beam is scanned along a predetermined raster line on the target plate of an X-ray tube to produce a moving point source of X-rays and wherein the region of the subject which is to be imaged is situated between the target plate and an X-ray detector (having a radiation-sensitive area smaller than the area of said target plate is situated on the opposite side of a subject to be imaged,) comprising the step of varying the rate of scanning movement of said electron beam along said predetermined raster line in a programmed manner dependent on the position of a momentary point of impact of said electron beam on said target plate relative to the position of a fixed specific point on said predetermined raster line. (as a function of the distance of the point of impact of said electron beam on said target plate from the specific point on said predetermined raster line which is closest to said detector.)

2. A method as defined in claim 1 wherein said electron beam is successively scanned along a plurality of additional raster lines each displaced from the preceding raster line in a direction normal to said predetermined raster line, comprising the further step of varying the displacement of each of said additional raster lines from the preceding one thereof as a function of distance from said predetermined raster line.

3. A method as defined in claim 1 wherein said electron beam is successively scanned along a plurality of additional raster lines each displaced from the preceding raster line in a direction normal to said predetermined raster line, including the step of progressively varying the displacement of each of said plurality of additional raster lines from the preceding one thereof as a function of the distance of the momentary point of impact of said electron beam on said target plate from said fixed specific point as taken along a direction parallel to said predetermined raster line.

4. A method as defined in claim 1 wherein said subject to be imaged is of arcuate configuration and is positioned with the center of curvature thereof substantially at said detector, wherein said step of progressively varying the rate of scanning movement of said electron beam along said predetermined raster line as a function of the distance of the momentary point of impact of said electron beam on said target plate from said fixed specific point where said fixed specific point is the origin of the shortest ray path between said momentary point of impact of said electron beam on said target and said detector includes varying said rate of scanning movement along said predetermined raster line as a function of the tangent of an angle $\theta$ wherein $\theta$ is the angle defined by a line extending from said fixed specific point to said detector and another line extending from said point of impact of said electron beam on said target plate to said detector.

5. A method for improving image quality in a scanning X-ray system wherein an electron beam is scanned along a first raster line on a target plate of an X-ray tube to produce a moving point source of X-rays and wherein the region of the subject which is to be imaged is situated between the target plate and an X-ray detector comprising the step of progressively increasing the electron beam current of said electron beam in a programmed manner dependent on the position of the momentary point of impact of said electron beam on said target plate relative to the position of a fixed specific point on said first raster line.

6. A method for improving image quality in a scanning X-ray system wherein an electron beam is scanned along a first raster line on a target plate to produce a moving point source of X-rays and wherein the region of the subject which is to be imaged is between the target plate and an X-ray detector comprising the step of varying the energy level of said electron beam in the course of the scanning action of said electron beam as a function of the position of the momentary point of impact of said electron beam on said target plate relative to a fixed specific point on said raster line to compensate for the unwanted variations of radiation flux level at the subject.

* * * * *